(12) United States Patent
Olson

(10) Patent No.: US 9,833,616 B2
(45) Date of Patent: Dec. 5, 2017

(54) SYSTEM AND METHOD FOR CARDIAC LEAD

(75) Inventor: Nathan Lee Olson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1988 days.

(21) Appl. No.: 12/649,197

(22) Filed: Dec. 29, 2009

(65) Prior Publication Data

US 2011/0004285 A1 Jan. 6, 2011

Related U.S. Application Data

(60) Provisional application No. 61/142,292, filed on Jan. 2, 2009.

(51) Int. Cl.
*A61N 1/00* (2006.01)
*A61N 1/05* (2006.01)
(Continued)

(52) U.S. Cl.
CPC ......... *A61N 1/056* (2013.01); *A61M 25/0054* (2013.01); *A61N 1/0488* (2013.01);
(Continued)

(58) Field of Classification Search
CPC .......... A61M 25/0032; A61M 25/0054; A61M 25/04; A61M 25/0013; A61N 1/056; A61N 1/3956; A61N 1/0488; A61N 1/36
See application file for complete search history.

(56) References Cited

U.S. PATENT DOCUMENTS

| 4,643,202 A | 2/1987 | Roche |
| 4,759,378 A | 7/1988 | Swendson et al. |

(Continued)

FOREIGN PATENT DOCUMENTS

| EP | 0343402 A2 | 11/1989 |
| EP | 661078 A2 | 7/1995 |

(Continued)

OTHER PUBLICATIONS

International Search Report and Written Opinion of the International Searching Authority regarding International Application No. PCT/US2009/069782, dated Sep. 3, 2010.

(Continued)

*Primary Examiner* — Lindsey G Wehrheim

(57) ABSTRACT

An implantable medical device (IMD) can include implantable pulse generator (IPG) devices, implantable cardioverter-defibrillators (ICD), cardiac resynchronization therapy defibrillator devices, neurostimulators or combinations thereof. In one example, the IMD can include a body assembly, which can provide at least one electrical signal corresponding to a therapy. The IMD can also include a cardiac lead assembly, which can have a proximal portion and a distal portion. The proximal portion of the cardiac lead assembly can be in communication with the body assembly to receive the therapy and the distal portion can be adapted to be coupled to an anatomical structure to transmit the at least one electrical signal to the anatomical structure. The proximal portion of the cardiac lead assembly can have a first stiffness and the distal portion can have a second stiffness. The first stiffness can be greater than the second stiffness.

10 Claims, 21 Drawing Sheets

(51) Int. Cl.
*A61N 1/04* (2006.01)
*A61N 1/36* (2006.01)
*A61N 1/39* (2006.01)
*A61M 25/00* (2006.01)
*A61M 25/04* (2006.01)

(52) U.S. Cl.
CPC ..... *A61M 25/0013* (2013.01); *A61M 25/0032* (2013.01); *A61M 25/04* (2013.01); *A61N 1/36* (2013.01); *A61N 1/3956* (2013.01)

(56) References Cited

U.S. PATENT DOCUMENTS

| | | |
|---|---|---|
| 5,807,354 A | 9/1998 | Kenda |
| 5,897,537 A | 4/1999 | Berg et al. |
| 5,935,159 A | 8/1999 | Cross, Jr. et al. |
| 5,967,977 A | 10/1999 | Mullis et al. |
| 6,181,971 B1 | 1/2001 | Doan |
| 6,188,931 B1 | 2/2001 | Holmstrom et al. |
| 6,193,743 B1 | 2/2001 | Brayton et al. |
| 6,249,709 B1 | 6/2001 | Conger et al. |
| 6,253,111 B1 | 6/2001 | Carner |
| 6,259,954 B1 | 7/2001 | Conger et al. |
| 6,278,897 B1 | 8/2001 | Rutten et al. |
| 6,289,250 B1 | 9/2001 | Tsuboi et al. |
| 6,321,102 B1 | 11/2001 | Spehr et al. |
| 6,324,415 B1 | 11/2001 | Spehr et al. |
| 6,374,142 B1 | 4/2002 | Skinner et al. |
| 6,374,488 B1 | 4/2002 | McLean et al. |
| 6,377,857 B1 | 4/2002 | Brayton et al. |
| 6,381,835 B1 | 5/2002 | Conger et al. |
| 6,445,958 B1 | 9/2002 | Machek et al. |
| 6,456,890 B2 | 9/2002 | Pianca et al. |
| 6,477,428 B1 | 11/2002 | Skinner et al. |
| 6,477,429 B1 | 11/2002 | Conger et al. |
| 6,505,401 B1 | 1/2003 | Doan |
| 6,544,270 B1 | 4/2003 | Zhang |
| 6,564,107 B1 | 5/2003 | Bodner et al. |
| 6,580,949 B1 | 6/2003 | Tsuboi et al. |
| 6,606,522 B2 | 8/2003 | Schell |
| 6,650,921 B2 | 11/2003 | Spehr et al. |
| 6,650,945 B2 | 11/2003 | Helland et al. |
| 6,654,270 B2 | 11/2003 | Osaka et al. |
| 6,662,055 B1 | 12/2003 | Prutchi |
| 6,671,553 B1 | 12/2003 | Helland et al. |
| 6,687,549 B1 | 2/2004 | Helland et al. |
| 6,701,191 B2 | 3/2004 | Schell |
| 6,748,277 B1 | 6/2004 | Chitre et al. |
| 6,792,316 B2 | 9/2004 | Sass |
| 6,792,317 B1 | 9/2004 | Doan et al. |
| 6,925,334 B1 | 8/2005 | Salys |
| 6,950,710 B2 | 9/2005 | Shirakawa et al. |
| 6,968,237 B2 | 11/2005 | Doan et al. |
| 6,973,351 B2 | 12/2005 | Morgan |
| 6,978,185 B2 | 12/2005 | Osypka |
| 6,999,821 B2 | 2/2006 | Jenney et al. |
| 7,010,358 B1 | 3/2006 | Kroll et al. |
| 7,013,182 B1 | 3/2006 | Krishnan |
| 7,020,529 B2 | 3/2006 | Krall et al. |
| 7,127,302 B2 | 10/2006 | Palm |
| 7,155,293 B2 | 12/2006 | Westlund et al. |
| 7,158,837 B2 | 1/2007 | Osypka et al. |
| 7,174,220 B1 | 2/2007 | Chitre et al. |
| 7,191,017 B1 | 3/2007 | Koop et al. |
| 7,212,868 B2 | 5/2007 | McAuliffe et al. |
| 7,231,259 B2 | 6/2007 | Jenney et al. |
| 7,238,883 B2 | 7/2007 | Zarembo |
| 7,239,923 B1 | 7/2007 | Tockman et al. |
| 7,257,449 B2 | 8/2007 | Bodner |
| 7,280,875 B1 | 10/2007 | Chitre et al. |
| 7,305,270 B1 | 12/2007 | Kroll et al. |
| 7,353,066 B1 | 4/2008 | Chitre et al. |
| 7,369,901 B1 | 5/2008 | Morgan et al. |
| 7,383,091 B1 | 6/2008 | Chitre et al. |
| 8,332,045 B2 | 12/2012 | Sommer et al. |
| 2001/0037136 A1 | 11/2001 | Pianca et al. |
| 2002/0004635 A1* | 1/2002 | Yock ............... 600/467 |
| 2002/0035319 A1 | 3/2002 | Spehr et al. |
| 2002/0072737 A1* | 6/2002 | Belden et al. ........ 606/34 |
| 2002/0147488 A1 | 10/2002 | Doan et al. |
| 2002/0183821 A1 | 12/2002 | Schell |
| 2003/0023294 A1 | 1/2003 | Krall et al. |
| 2003/0105505 A1 | 6/2003 | Pianca |
| 2003/0139794 A1 | 7/2003 | Jenney et al. |
| 2003/0217463 A1 | 11/2003 | Schmidt et al. |
| 2004/0054390 A1 | 3/2004 | Zarembo et al. |
| 2004/0147993 A1 | 7/2004 | Westlund et al. |
| 2004/0230277 A1 | 11/2004 | Schell |
| 2005/0065587 A1 | 3/2005 | Gryzwa |
| 2005/0080471 A1 | 4/2005 | Chitre et al. |
| 2005/0131507 A1 | 6/2005 | Sundberg |
| 2005/0222660 A1 | 10/2005 | McAuliffe et al. |
| 2005/0228469 A1 | 10/2005 | Zarembo et al. |
| 2005/0228470 A1 | 10/2005 | Osypka |
| 2006/0074471 A1 | 4/2006 | Palm |
| 2006/0095107 A1 | 5/2006 | Osypka |
| 2006/0190067 A1 | 8/2006 | Wengreen et al. |
| 2006/0282144 A1 | 12/2006 | Knapp et al. |
| 2006/0293737 A1 | 12/2006 | Krishnan |
| 2007/0038278 A1 | 2/2007 | Zarembo |
| 2007/0142890 A1 | 6/2007 | Zarembo et al. |
| 2007/0156216 A1 | 7/2007 | McAuliffe et al. |
| 2007/0225786 A1 | 9/2007 | Bly et al. |
| 2007/0282414 A1* | 12/2007 | Soltis et al. .......... 607/122 |
| 2007/0282415 A1 | 12/2007 | Tockman et al. |
| 2008/0046059 A1 | 2/2008 | Zarembo et al. |
| 2008/0132985 A1 | 6/2008 | Wedan et al. |
| 2008/0183263 A1* | 7/2008 | Alexander ........... 607/122 |

FOREIGN PATENT DOCUMENTS

| | | |
|---|---|---|
| EP | 1033144 A1 | 9/2000 |
| WO | 8002231 A1 | 10/1980 |
| WO | WO-9953993 A1 | 10/1999 |
| WO | WO-0102053 A1 | 1/2001 |
| WO | WO-2008051913 A1 | 5/2008 |
| WO | 2008107869 A1 | 9/2008 |

OTHER PUBLICATIONS

International Search Report and Written Opinion of the International Searching Authority regarding International Application No. PCT/US2009/069781, dated Nov. 5, 2010.

\* cited by examiner

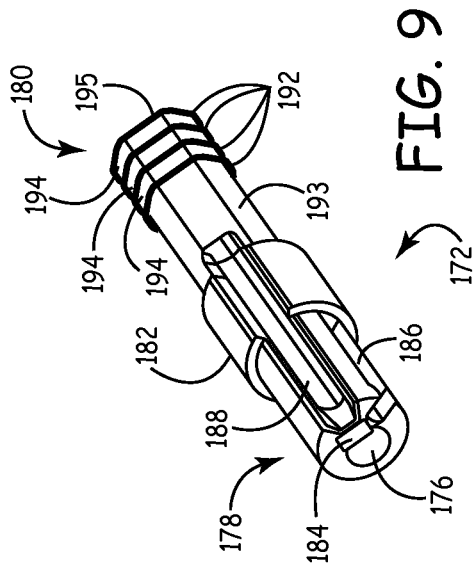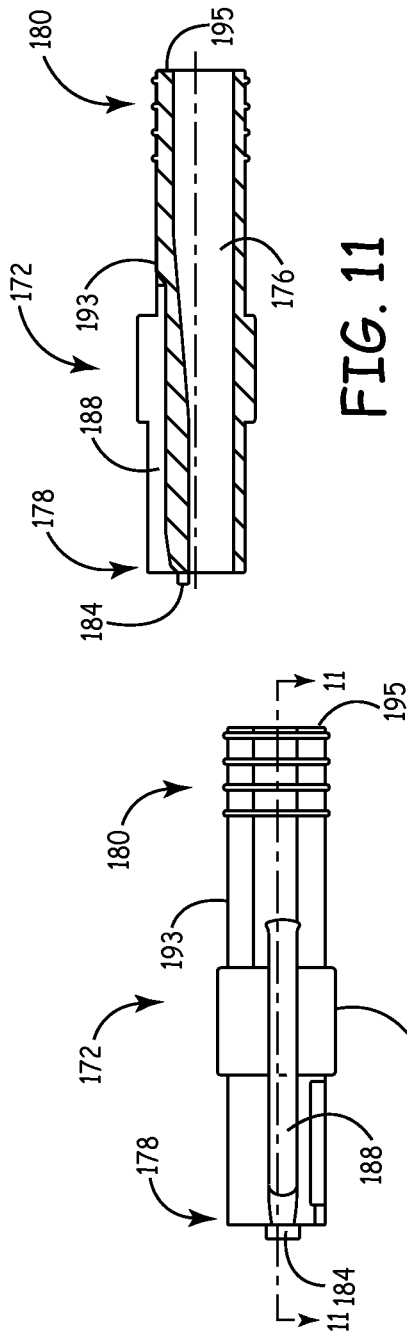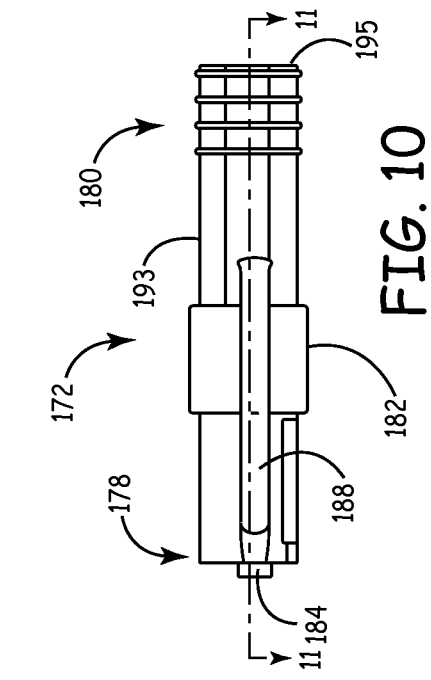

SYSTEM AND METHOD FOR CARDIAC LEAD

CROSS-REFERENCE TO RELATED APPLICATIONS

This application claims the benefit of U.S. Provisional Application No. 61/142,292, filed on Jan. 2, 2009. The entire disclosure of the above application is incorporated herein by reference.

INTRODUCTION

This section provides background information related to the present disclosure which is not necessarily prior art.

The human anatomy includes many types of tissue that can either voluntarily or involuntarily perform certain functions. For example, the cardiac or heart muscle involuntarily contracts to propel blood from atria and ventricles to blood vessels of the circulatory system. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with implantable medical devices (IMDs). These devices can include implantable pulse generator (IPG) devices, pacemakers, implantable cardioverter-defibrillator (ICD) devices, cardiac resynchronization therapy defibrillator devices, or combinations thereof.

One of the main portions of the IMD can include a lead that may be directly connected to tissue to be affected by the IMD (e.g., a muscle bundle). The lead can include a tip portion that may be directly connected to the anatomical tissue and a lead body that is connected to the device body or therapeutic driving device. It may be generally known that the device body or case portion can be implanted in a selected portion of the anatomical structure, such as in a chest or abdominal wall. In this case, the lead can be inserted through various venous portions so that the tip portion can be selectively positioned near or in the muscle group.

The present disclosure relates to implantable medical devices (IMDs), and in particular to a system and method for a cardiac lead system having a support structure.

SUMMARY

Provided is an implantable medical device. The implantable medical device can include a body assembly, which can provide at least one electrical signal corresponding to a therapy. The implantable medical device can also include a cardiac lead assembly, which can have a proximal portion and a distal portion. The proximal portion of the cardiac lead assembly can be in communication with the body assembly to receive the therapy and the distal portion can be adapted to be coupled to an anatomical structure to transmit the at least one electrical signal to the anatomical structure. The proximal portion of the cardiac lead assembly can have a first stiffness and the distal portion can have a second stiffness. The first stiffness can be greater than the second stiffness.

Further provided is an implantable medical device. The implantable medical device can include a cardiac lead having at least one multilumen member with a proximal portion, a distal portion, and a transition zone therebetween. The proximal portion of the at least one multilumen member can be adapted to be in communication with another implantable medical device and the distal portion can be adapted to be in communication with an anatomical structure. The implantable medical device can also include at least one electrode assembly coupled to the at least one multilumen member to transmit electrical signals from the other implantable medical device to the anatomical structure. The implantable medical device can include a support structure, which can be coupled to the proximal portion. The support structure can provide increased hoop strength to the proximal portion of the at least one multilumen member relative to the distal portion.

An implantable medical device is also provided. The implantable medical device can include a body assembly. The body assembly can transmit at least one electrical signal to treat an anatomical structure and can be adapted to receive at least one signal from the anatomical structure. The implantable medical device can include a cardiac lead in communication with the body assembly to enable communication between the body assembly and the anatomical structure. The cardiac lead including at least one multilumen member with a proximal portion, a distal portion, and a transition zone therebetween. The proximal portion can be coupled to the body assembly and the distal portion can be adapted to be coupled to the anatomical structure. The at least one multilumen member can also have a plurality of conduits. The implantable medical device can include a plurality of electrode assemblies, which can be coupled to the at least one multilumen member. Each of the plurality of electrode assemblies can have a transmission member in communication with the body assembly to communicate electrical signals. Each one of the plurality of transmission members can be received within a respective one of the plurality of conduits. The implantable medical device can also include a plurality of jumper members, with one of the plurality of jumper members disposed over one of the plurality of transmission members at the transition zone to enable the plurality of transmission members to transition from the proximal portion of the at least one multilumen member to the distal portion. Thus, the transition zone can optimize the performance of the conductors by allowing the implantable medical device to adapt to the surrounding anatomical structure.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 9 is a perspective view of a first sleeve of the ring electrode assembly of FIG. 8A;

FIG. 10 is a side view of the first sleeve of FIG. 9;

FIG. 11 is a cross-sectional view of the first sleeve of FIG. 9, taken along line 11-11 of FIG. 10;

Corresponding reference numerals indicate corresponding parts throughout the several views of the drawings.

DETAILED DESCRIPTION

Figure 1:
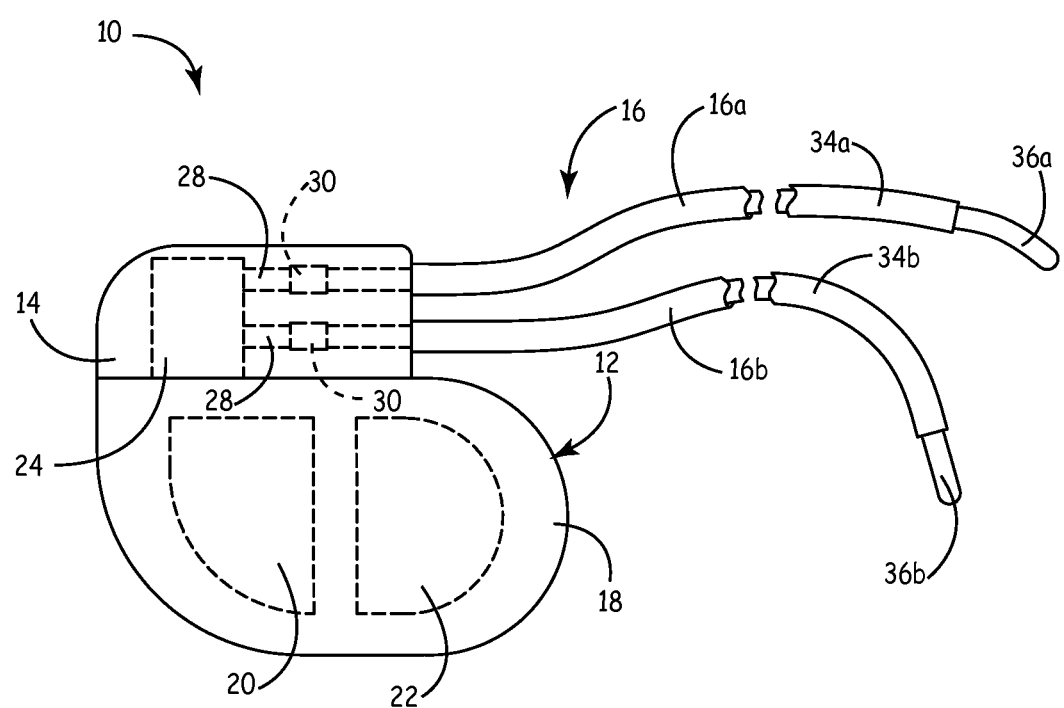
FIG. 1 is a schematic view of an implantable medical device (IMD) including a lead assembly interconnected with a device body.

Example embodiments will now be described more fully with reference to the accompanying drawings.

The following description may be merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for relieving strain experienced by a cardiac lead system. It should be noted, however, that the present teachings could be applicable to any appropriate procedure in which it can be desirable to relieve strain in a multi-lumen structure. Therefore, it will be understood that the following discussions are not intended to limit the scope of the appended claims.

With reference to FIG. 1, an implantable medical device (IMD) 10, which can include implantable pulse generator (IPG) devices, implantable cardioverter-defibrillator (ICD) devices, cardiac resynchronization therapy defibrillator devices, neurostimulators or combinations thereof, can be exemplarily illustrated. The IMD 10 can include an implantable body assembly or case 12, a connector assembly 14, and at least one cardiac lead assembly 16. While the connector assembly 14 is illustrated as a separate element fastened to the body assembly 12, it should also be understood that the body assembly 12 and the connector assembly 14 can be integrally formed. Accordingly, the implantable body assembly 12 and the connector assembly 14 can be formed of appropriate materials and include appropriate features, such as a hermetically sealed body wall 18. The body wall 18 can be made of a substantially inert material or of a conducting material.

Contained within the body wall 18 and/or otherwise associated with the body assembly 12 can be a power device 20 (e.g., battery) and a controller assembly 22. The controller assembly 22 can include a circuit board having a processor, memory, transmitter, receiver, and other appropriation portions, further discussed herein.

An interconnection mechanism 24, located between the body assembly 12 and the connector assembly 14 can convey power from the power device 20 and signals from the controller assembly 22 to the connector assembly 14. In this way, the controller assembly 22 can provide signals to the other components of the IMD 10 for operation. In particular and for example, the processor (not shown) of the controller assembly 22 can provide signals to the IMD 10 to indicate precise timing for driving an electrical current for pacing the heart.

The connector assembly 14 can extend from or be integrated with the body assembly 12, as previously described. The connector assembly 14 can include multiple ports 28 that each interconnect with a connector terminal 30 of the lead assembly 16. For example, FIG. 1 schematically illustrates first and second lead assemblies 16a, 16b where each lead assembly 16a, 16b includes lead bodies 34a, 34b terminating at tip electrodes 36a, 36b. Although the IMD 10 can be illustrated in FIGS. 1 and 2 as including two lead assemblies 16a, 16b terminating at tip electrodes 36a, 36b, it will be understood that any number of lead assemblies 16 and any number or location of electrodes 36 could be employed with the IMD 10 depending upon the malady of a patient 40 and the particular IMD 10 employed. A majority of each lead body 34a, 34b can also be formed in a generally known and selected manner. For example, the various conductors and electrical components can be encased in silicone, polyurethane, and other appropriate materials.

Moreover, a support structure 152 (FIG. 5) and/or a fixation member 166 (FIG. 4) as further discussed herein can be associated with one or all of the lead assemblies 16a, 16b for the particular IMD 10 employed. In brief, the support structure 152 can be used to stiffen the lead assembly 16 for providing strain relief during bending. The fixation member 166 can also be included with each lead assembly 16a, 16b to affix each tip electrode 36a, 36b relative to or in a selected tissue of the patient 40 as will be discussed herein. The fixation member 166 can be near each tip electrode 36a, 36b or define a portion of the tip electrode 36a, 36b. Fixation members 166 can be of any appropriate type, including a grapple mechanism, a helical mechanism, a drug-coated connection mechanism, and other appropriate connection mechanisms.

Figure 2:
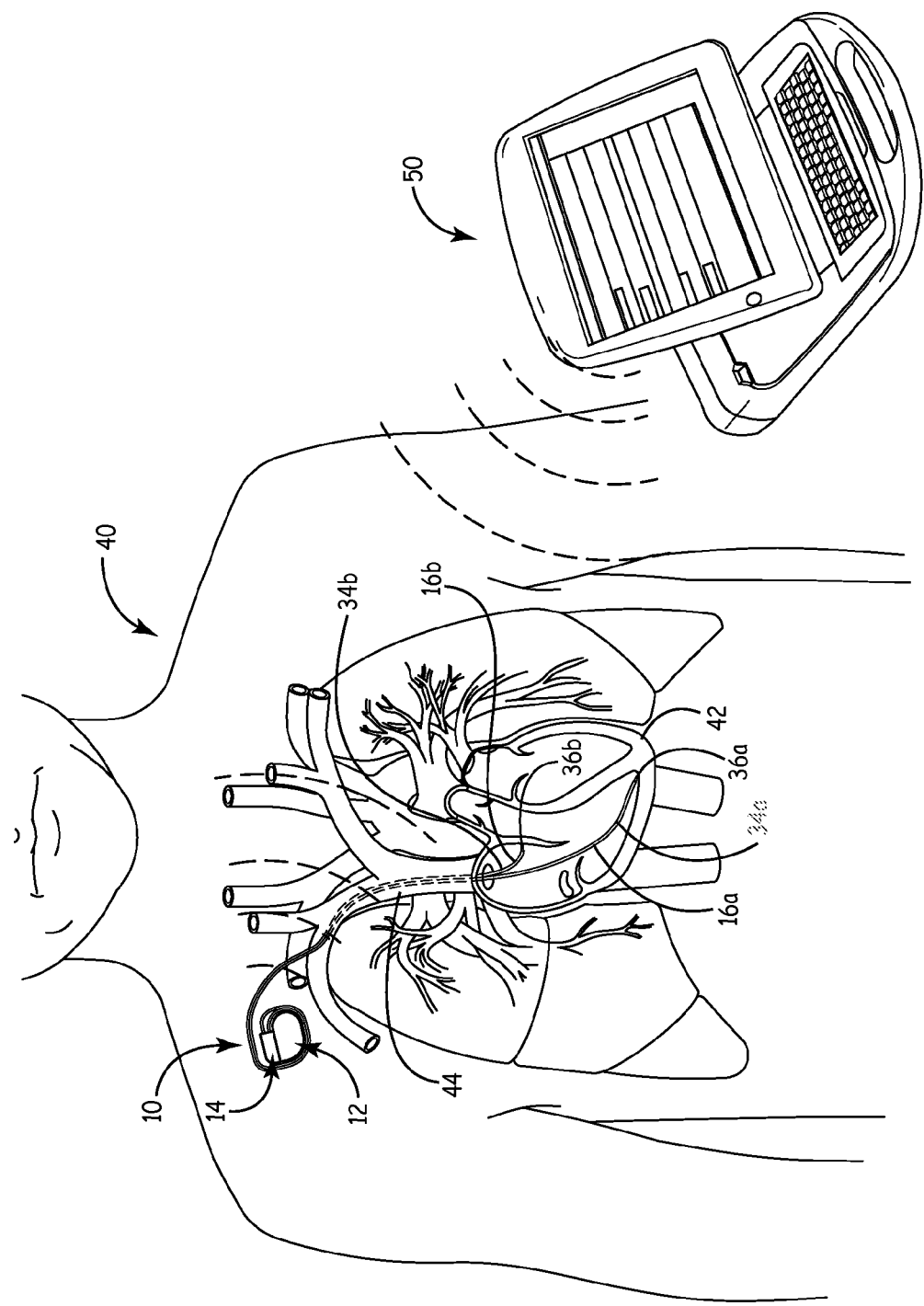
FIG. 2 is a simplified environmental view of the IMD implanted within a patient.

The IMD 10, including the components discussed above, can be implanted in the patient 40 as illustrated in FIG. 2. In one example, the IMD 10 can include the first lead assembly 16a and the second lead assembly 16b. The first and second lead assemblies 16a, 16b can be connected to the connector assembly 14. As one skilled in the art will understand, the position of the lead bodies 34a, 34b of the lead assemblies 16a, 16b can depend upon the type of IMD 10 and the malady of the patient 40. For example, the lead assemblies 16a, 16b can be positioned transvenously to positions within a heart 42 or on the outside of the heart 42 of the patient 40. The IMD 10 can be provided to control and monitor the heart 42, such as, to pace the heart 42, defibrillate the heart 42, sense conditions of the heart 42, etc.

The IMD 10, including the body assembly 12, the connector assembly 14, and the first and second lead assemblies 16a, 16b, can be implanted using known procedures. For example, an incision can be made in a chest wall or an abdomen wall of the patient 40 and the lead assemblies 16a, 16b can be passed through selected veins to selected portions of the heart 42 of the patient 40. The body assembly 12 can also be positioned through the incision into a chest wall or abdominal wall of the patient 40. In a selected procedure, the lead assemblies 16a, 16b can be passed through a superior vena cava 44 of the patient 40. The lead tips or tip electrodes 36a, 36b can be positioned at various positions in the heart 42, such as at the ventricles or atriums thereof. The position of the lead assemblies 16a, 16b and tip electrodes 36a, 36b can be selected for pacing, defibrillation, sensing, or other appropriate procedures. The specific implantation procedure, position of the tip electrodes 36a, 36b, and the like can depend upon the patient 40, the surgeon performing the procedure, the specifics of the lead assemblies 16a, 16b, and/or other considerations.

As discussed above, the IMD 10, including the body assembly 12 and the lead assemblies 16a, 16b can include various features or controls to defibrillate or pace the heart 42, generally indicated as the controller assembly 22 (shown schematically in FIG. 1). The controller assembly 22 can include a processor (not shown) which can be located within the body assembly 12. The controller assembly 22 can be programmed to control driving of a current through the lead bodies 34a, 34b to the tip electrodes 36a, 36b to pace the heart 42.

With continued reference to FIG. 2, a programming system or programmer 50 can be provided. The programmer 50 can include a telemetry system (not shown) that can be operable to wirelessly transmit a signal to the controller assembly 22 within the body assembly 12. It will be understood that a wired communication system can also be used. In addition, an induction system (not shown) can be used wherein a coil can be positioned near the body assembly 12 and a signal can be sent from the programmer 50 via induction. The programmer 50 can also receive information from the IMD 10 (e.g., tachycardia rhythms, times, and programming settings) to assist in providing an appropriate program for therapy and to determine if the IMD 10 is operating properly. The programmer 50 can include any appropriate programming system, including one generally known to those skilled in the art, such as the Medtronic CARELINK™ programmer, sold by Medtronic, Inc. of Minneapolis, Minn.

Moreover, the IMD 10, including the body assembly 12 and the lead assemblies 16a, 16b, can be formed to counteract or interact with various environmental factors. For example, the lead assemblies 16a, 16b can include features or portions to re-direct or dissipate thermal energy created by an induced current. Induced currents can be created due to an external field, such as an electromagnetic field acting on the conductors of the lead assemblies 16a, 16b. In addition, the lead assemblies 16a, 16b can be formed to relieve strain associated with the bending of the lead assemblies 16a, 16b within the anatomy.

Figure 3:
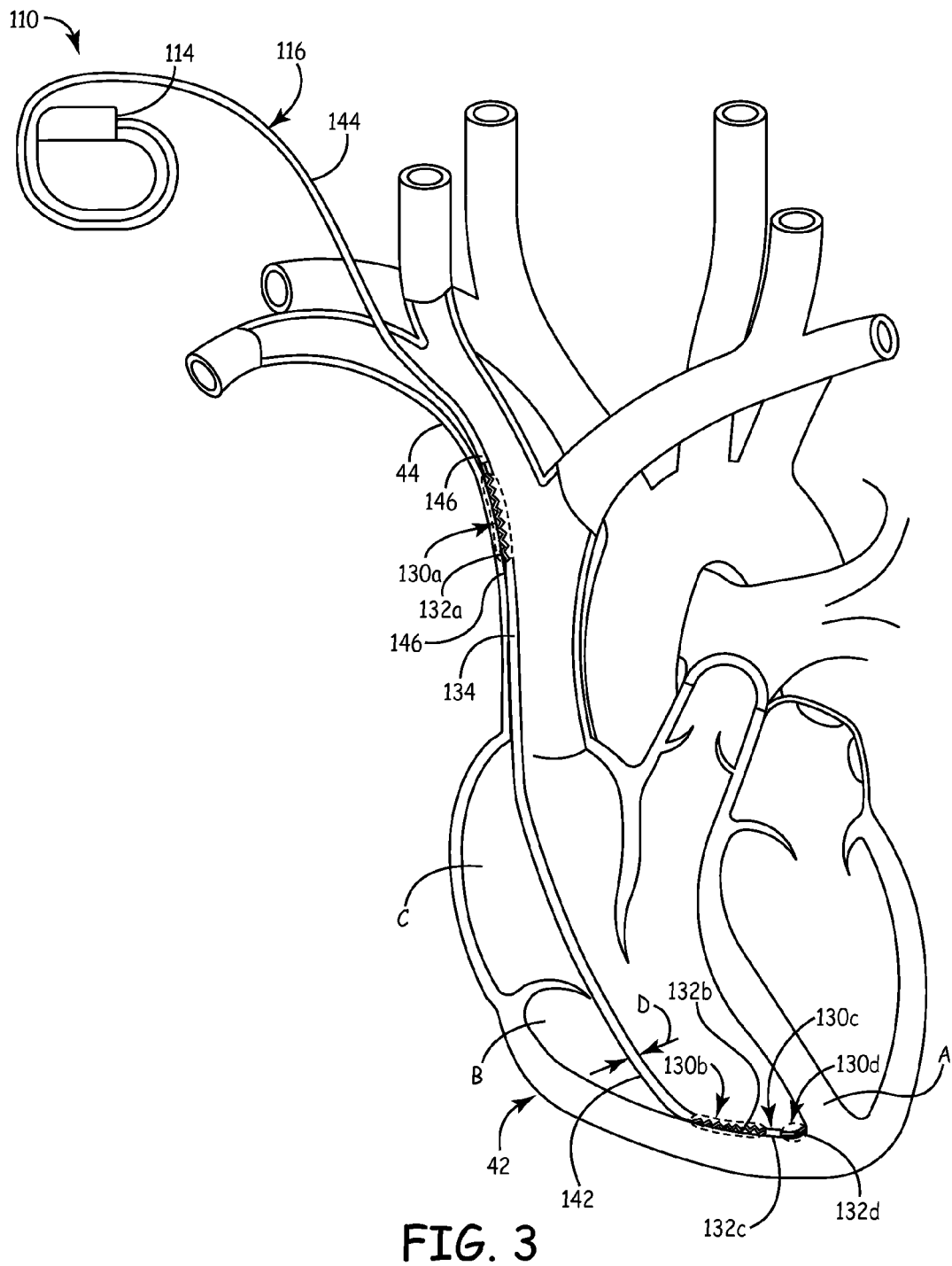
FIG. 3 is a schematic environmental view of an implantable cardioverter-defibrillator (ICD) implanted in the patient.

For example, according to various exemplary embodiments, with reference to FIG. 3, the IMD 10 can comprise an implantable cardiac device, such as an implantable cardioverter-defibrillator (ICD) 110. As the ICD 110 that will be described herein with reference to FIGS. 3-16 can be similar to the IMD 10 described with reference to FIGS. 1 and 2, similar reference numerals will be used to denote like components.

With continued reference to FIG. 3, the ICD 110 can be used to detect and treat cardiac arrhythmias, and thus, can deliver a therapy to a desired location within the heart 42. In this regard, the ICD 110 can provide anti-tachycardia pacing, cardioversion, defibrillation, and/or bradycardia pacing, while also monitoring the heart rhythm to determine if a therapy may be needed. As the ICD 110 can comprise any suitable ICD, such as the ENTRUST™ family of ICDs available from Medtronic, Inc. of Minneapolis, Minn., the ICD 110 will not be discussed in great detail herein. Briefly, however, the ICD 110 can include at least one ICD lead assembly 116, which can be implanted into an anatomical structure, such as the heart 42. Generally, the lead assembly 116 can comprise a high voltage lead assembly. The ICD 110 can comprise a single chamber having one lead assembly 116 (as illustrated), a dual chamber having two lead assemblies 116 or a biventricular having three lead assemblies 116. In any case, each lead assembly 116 can both sense electrical activity of the heart 42 and/or can deliver electrical energy to pace the heart 42.

As will be discussed further herein, with reference to FIGS. 3-16, each lead assembly 116 can include at least one electrode assembly 130, which can include an associated electrode 132 and a transmission member 136, comprising an inner conductor 138 and an insulative member 140. The at least one inner conductor 138 of the transmission member 136 can extend from each connector terminal 30 to engage the associated electrode 132. Briefly, the electrode 132 can be in communication with the inner conductor 138 to receive a therapy, such as an electrical pulse, and can be in contact with the anatomical structure to deliver the therapy to the anatomical structure or heart 42. Thus, the inner conductor 138 can be in electrical communication with the electrode 132 and the ICD 110 to receive the therapy. The inner conductor 138 can be encased by or coated with the insulative member 140, such as a biocompatible polymer, for example, a fluoropolymer. In this way, the insulative member 140 surrounding the inner conductor 138 electrically insulates the inner conductor 138 from the external environment for promoting this electrical communication. The inner conductor 138 can also be cannulated or include a solid or non-cannulated cable. It will also be understood by one skilled in the art that the inner conductor 138 can be one-piece or multiple components that are interconnected. Also, more than one inner conductor 138 can be provided, such as one inner conductor 138 for each electrode 132 in each lead assembly 116. Furthermore, although the inner conductor 138 and insulative member 140 may be omitted from the drawings for the sake of clarity, it will be understood that each electrode 132 is in communication with at least one inner conductor 138, which is surrounded by a respective insulative member 140.

Figure 4:
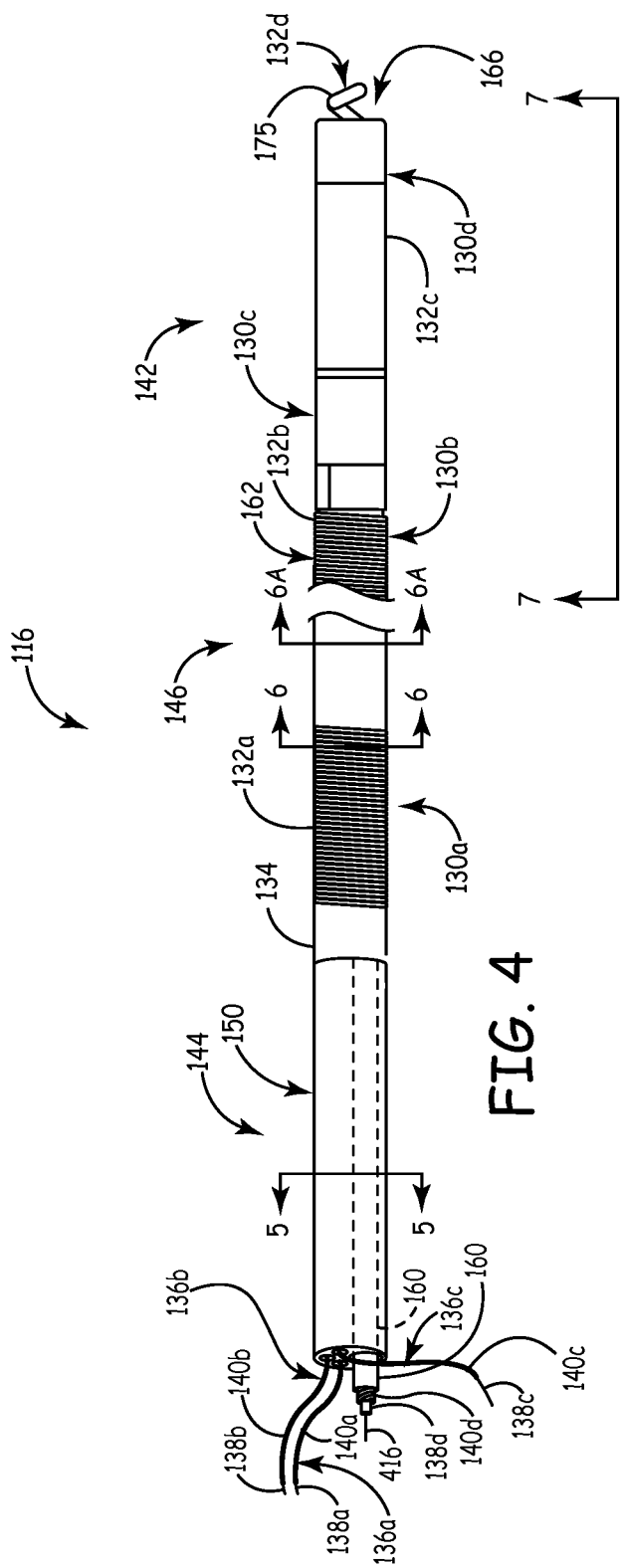
FIG. 4 is a perspective schematic view of one of various exemplary lead assemblies according to the present teachings.
Figure 5:
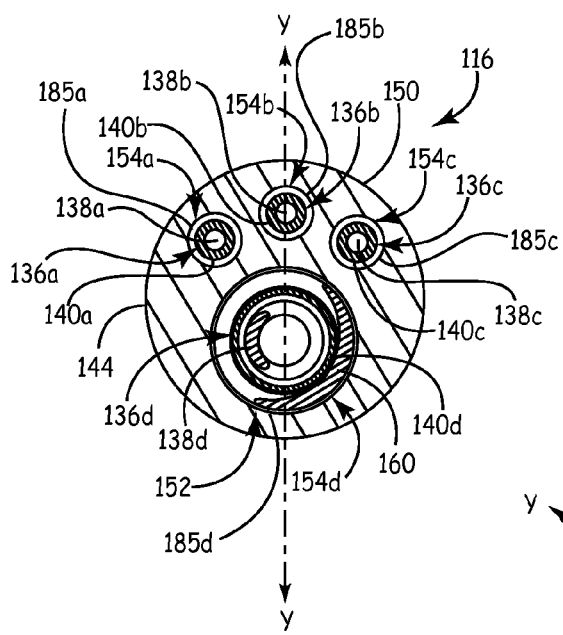
FIG. 5 is a cross-sectional view of the lead assembly of FIG. 4, taken along line 5-5 of FIG. 4.

Referring now to FIGS. 3-5 and in this example, the lead assembly 116 can include four electrode assemblies 130 (e.g., first electrode assembly 130a, second electrode assembly 130b, third electrode assembly 130c, and fourth electrode assembly 130d) which can be coupled to the lead assembly 116 in any known manner. It should be noted that while the lead assembly 116 may be illustrated with four electrode assemblies 130 in FIG. 3, the lead assembly 116 may have any number of electrode assemblies 130. The lead assembly 116 can serve to protect, carry, and guide the at least one electrode assembly 130 through the anatomical structure.

The lead assembly 116 can have a lead body 134 that includes a distal portion or end 142, a proximal portion or end 144, a transition zone 146, which can transition the lead body 134 of the lead assembly 116 between the proximal end 144 and the distal end 142, a first multilumen tubing member 150, and the support structure 152. In one example, the proximal end 144 of the lead assembly 116 can interact with a connector assembly 114. As the connector assembly 114 can be generally known, the connector assembly 114 will not be discussed in great detail herein. Briefly, however, the connector assembly 114 can electrically couple the lead assembly 116 to the ICD 110 through the connector terminal 30 (as shown in FIG. 1). The connector assembly 114 can also be coupled to the first multilumen member 150.

Generally, with continued reference to FIGS. 4 and 5, the first multilumen member 150 can be composed of a biocompatible material, such as a biocompatible polymer, for example, a silicone rubber. In one example, the first multilumen member 150 can comprise a biocompatible polymer with additional structural support or stiffness, such as a high molecular weight polyurethane based polymer, a high molecular weight silicone or combinations thereof. The additional structural support in the composition of the first multilumen member 150 can further stiffen the proximal end 144 of the lead assembly 116.

With reference to FIG. 5, the first multilumen member 150 can include at least one separate proximal conduit 154 for each inner conductor 138 associated with the electrode assemblies 130, and for example, the first multilumen member 150 can comprise a first proximal conduit 154a, a second proximal conduit 154b, a third proximal conduit 154c, and a fourth proximal conduit 154d. In this example, the first, second, and third proximal conduits 154a, 154b, 154c can have a diameter that may be smaller than a diameter of the fourth proximal conduit 154d. Typically, the proximal conduits 154 can be positioned within the first multilumen member 150 such that the first multilumen member 150 can be symmetric with respect to an axis Y. The proximal conduits 154 can receive each of the inner conductors 138 of the electrode assemblies 130 to guide each of the inner conductors 138 from the ICD 110 to the electrode 132 of the respective electrode assembly 130.

Figure 6:
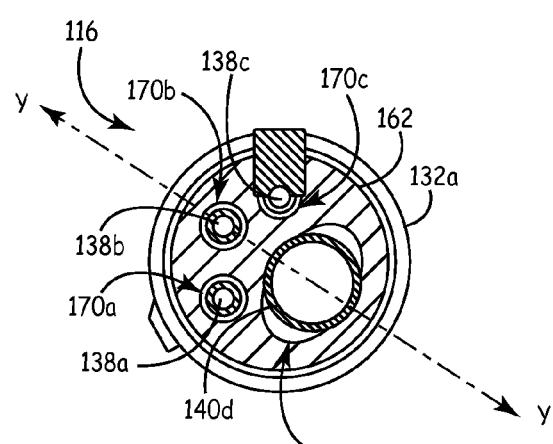
FIG. 6 is a cross-sectional view of the lead assembly of FIG. 4 taken along line 6-6 of FIG. 4.
Figure 7:
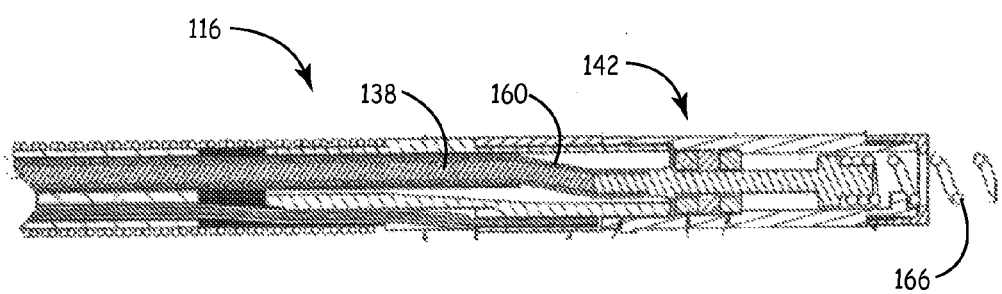
FIG. 7 is a cross-sectional view of the lead assembly of FIG. 4 taken along line 7-7 of FIG. 4.

With reference to FIGS. 4-6, the support structure 152 can stiffen the proximal end 144 of the first multilumen member 150, and can provide strain relief in the case that the proximal end 144 may be bent or flexed. In one example, the support structure 152 can comprise a conductive support coil 160. By employing the conductive support coil 160, the support structure 152 can serve as a redundant electrical path for one or more of the conductors 138 and/or could comprise an electrical shield for the lead assembly 116, such as that disclosed in commonly assigned U.S. Ser. No. 61/035,950, filed on Mar. 12, 1888, incorporated herein by reference. It should be noted, however, that the support structure 152 could comprise any suitable supporting device, such as a polymer tubing, braided sheath, polymer coil or sheath, etc.

The support coil 160 can extend from the connector assembly 114 to the transition zone 146. In one example, the support coil 160 can be secured within the fourth proximal conduit 154d at each end of the fourth proximal conduit 154d, via an adhesive, for example. Alternatively, however, the support coil 160 could be secured via any suitable means, such as fasteners. The support coil 160 can generally be formed to have a diameter, which can enable the inner conductor 138 and insulative member 140 associated with the fourth proximal conduit 154d to pass therethrough, as will be discussed in greater detail herein.

Generally, the support coil 160 can provide resistance to crush and/or kinking. Typically, the support coil 160 can have a circular cross-section even during flexing, which can allow the support coil 160 to provide added hoop strength to any structure that passes within it. Generally, hoop strength is a physical property that describes the ability of a circular structure to withstand internal pressure, bending and crushing forces. In other words, hoop strength can comprise the resistance of a circular structure to circumferential stress. By employing the support coil 160 as a support structure, the support coil 160 can provide hoop strength while bending or flexing, unlike a cylindrical tube, which could kink or deform into an oval shape during bending. The hoop strength of the support coil 160 can be increased by modifying dimensional characteristics of the support coil 160 (e.g., increasing diameter), changing material (e.g., a stiffer material), adding support structures, relocating lumens, and/or combinations of the above. It should be noted that the support structure 152 could also be located on the outside of the first multilumen member 150 and/or a second multilumen member 162 to provide the same hoop strength for the entire body of the lead assembly 116. For example, the support structure 152 could be positioned between an overlay 164 and the second multilumen member 162, or the support structure 152 could be incorporated directly into the overlay 164.

With reference to FIGS. 3, 4, and 6, the distal end 142 of the lead assembly 116 can include the second multilumen tubing member 162, the electrode assemblies 130, the overlay 164, and the fixation member 166, if desired. Generally, the distal end 142 can terminate within the anatomical structure adjacent to the desired location for the delivery of the therapy, and generally, for example, can terminate adjacent to an apex of the heart 42 (e.g., apex A), a ventricle of the heart 42 (e.g., right ventricle B), or other chambers of the heart 42 (e.g., right atria C).

The second multilumen member 162 can extend from the transition zone 146 to the distal end 142 of the lead assembly 116. The second multilumen member 162 can be similar to the first multilumen member 150, but can be composed of a more flexible biocompatible material than the first multilumen member 150, such as a biocompatible polymer. In one example, the second multilumen member 162 can comprise a silicone, for example. It should also be noted that the second multilumen member 162 can also include a polymeric overlay, if desired, which can result in an isodiametric lead assembly. By being composed of a more flexible material, the distal end 142 of the lead assembly 116 can more easily bend within the anatomy, which in turn, enables the lead assembly 116 to more precisely track the confines of the anatomy.

Figure 6A:
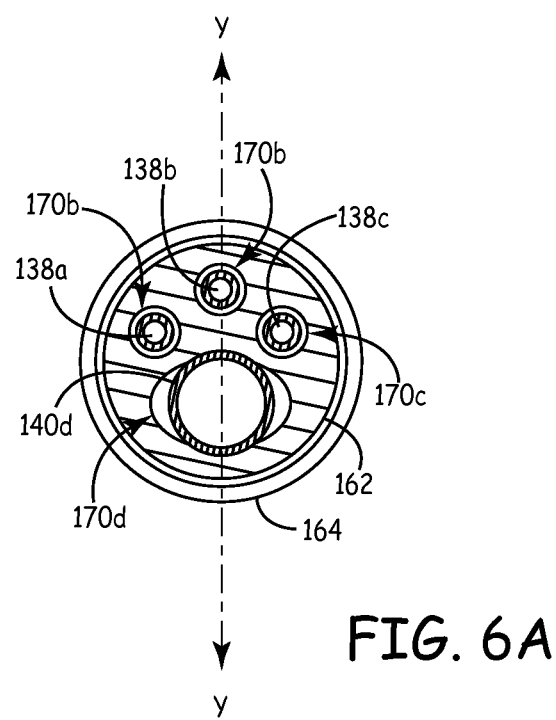
FIG. 6A is a cross-sectional view of the lead assembly of FIG. 4 taken along line 6A-6A of FIG. 4.

With reference to FIGS. 6 and 6A, the second multilumen member 162 can include at least one separate distal conduit 170 for each of the inner conductors 138 associated with the electrode assemblies 130. For example, the second multilumen member 162 can comprise the same number of distal conduits 170 as the proximal conduits 154 of the first multilumen member 150, such as a first distal conduit 170a, a second distal conduit 170b, a third distal conduit 170c, and a fourth distal conduit 170d, as will be discussed in greater detail herein. In this example, the first proximal conduit 154a can correspond to the first distal conduit 170a, the second proximal conduit 154b can correspond to the second distal conduit 170b, the third proximal conduit 154c can correspond to the third distal conduit 170c, and the fourth proximal conduit 154d can correspond to the fourth distal conduit 170d.

The first conduits 154a, 170a, the second conduits 154b, 170b, the third conduits 154c, 170c, and the fourth conduits 154d, 170d can have substantially similar diameters, so that the conductors 138 of the electrode assemblies 130 can pass through the lead assembly 116 in a uniform manner. It should also be understood that the fourth conduits 154d, 170d can have a different diameter, if desired, such as when the distal end 142 does not include the support structure 152. The distal conduits 170a, 170b, 170c, 170d can receive each of the inner conductors 138 of the electrode assemblies 130 to guide each of the inner conductors 138 from the ICD 110 to the electrode 132 of the respective electrode assembly 130.

With reference to FIGS. 3-7, selected ones of the electrode assemblies 130 can be operable to perform various specific tasks, such as delivering the therapy to the anatomical structure and/or sensing electrical activity at a desired site in the anatomical structure. In one example, the first and second electrode assemblies 130a, 130b can act as defibrillator electrode assemblies that assist in the function of delivering the therapy to the heart 42. The third electrode assembly 130c can act as a sense or ring electrode assembly that senses the electrical activity in the heart 42. The fourth electrode assembly 130d can act as a tip electrode assembly 130d that delivers the therapy to the desired site within the heart 42. As the structure of the electrode assemblies 130 may be generally known, and can be similar to the electrode assemblies associated with the SPRINT QUATTRO SECURE™ cardiac lead commercially available from Medtronic, Inc. of Minneapolis, Minn., they will not be discussed in great detail herein.

Briefly, however, the first defibrillator electrode assembly 130a can be disposed over and coupled to the second multilumen member 162, adjacent to or near the transition zone 146. The first defibrillator electrode assembly 130a can include a first defibrillator electrode 132a and a first transmission member 136a, which can comprise a first inner conductor 138a and a first insulative member 140a. Generally, the first defibrillator electrode assembly 130a can be coupled to the lead assembly 116 so that when the lead assembly 116 is implanted within the anatomical structure, such as the heart 42, the first defibrillator electrode 132a can be adjacent to the requisite portion of the anatomical structure to be sensed and/or treated, such as the superior vena cava 44, as may be generally known. The first defibrillator electrode 132a can be in communication with the first transmission member 136a The first transmission member 136a can pass through the first proximal conduit 154a of the first multilumen member 150 into the first conduit 170a of the second multilumen member 162, and can be in communication with and responsive to the ICD 110 to transmit an electrical signal or charge to the first defibrillator electrode 132a. The first transmission member 136a can include the first inner conductor 138a that can be encased by or coated with the insulative member 140a, such as a biocompatible polymer, for example, a fluoropolymer.

The second defibrillator electrode assembly 130b can be coupled to the second multilumen member 162 such that the second defibrillator electrode assembly 130b can be disposed between the first electrode assembly 130a and the ring electrode assembly 130c. The second defibrillator electrode assembly 130b can include a second defibrillator electrode 132b and a second transmission member 136b, which can comprise a second inner conductor 138b and a second insulative member 140b for the second defibrillator electrode 132b. Generally, the second defibrillator electrode assembly 130b can be coupled to the lead assembly 116 such that when the lead assembly 116 is implanted within the anatomical structure, such as the heart 42, the second defibrillator electrode 132b can be adjacent to a second portion of the anatomical structure, such as the right ventricle B of the heart 42 (FIG. 3). The second transmission member 136b can also pass through the second proximal conduit 154b of the first multilumen member 150 into the second conduit 170b of the second multilumen member 162, such that the second inner conductor 138b can be in communication with and responsive to the ICD 110 to transmit an electrical signal or charge to the second defibrillator electrode 132b. The second inner conductor 138b can be encased by or coated with the insulative member 140b, which can comprise a biocompatible polymer, and for example, a fluoropolymer.

Figure 8A:
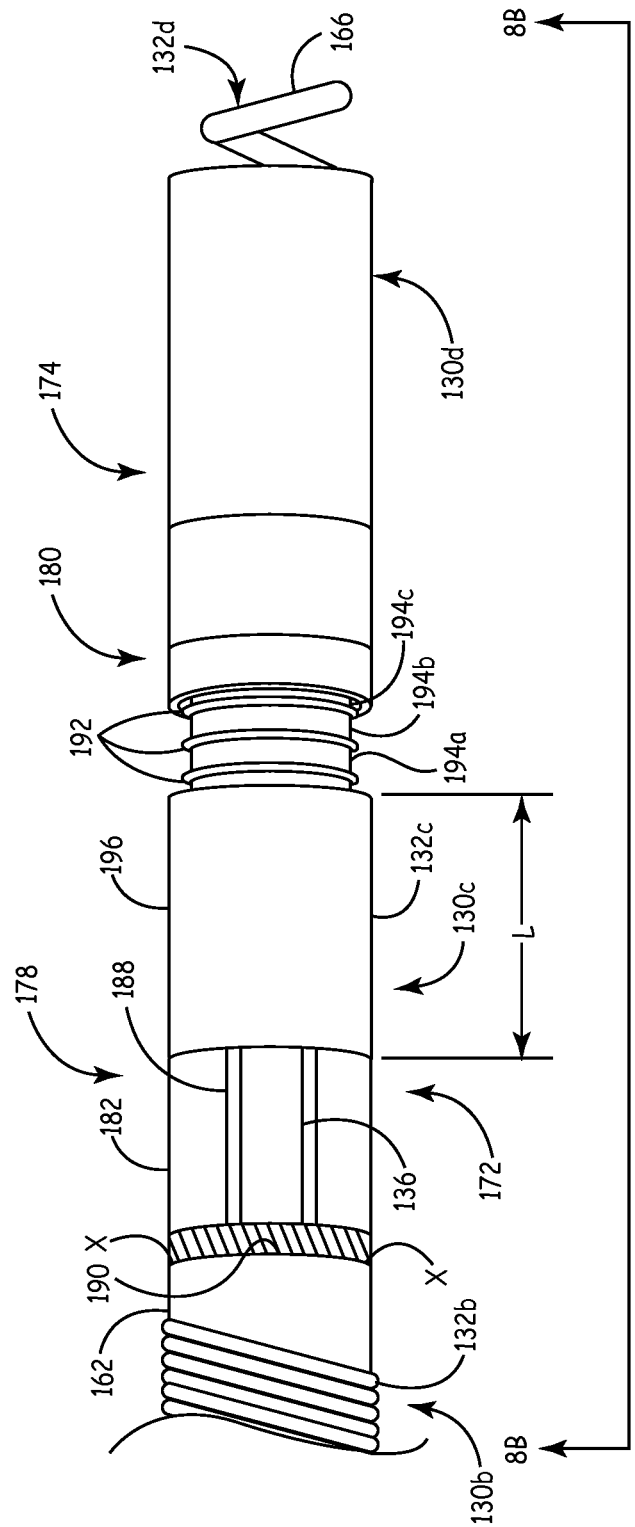
FIG. 8A is a schematic view of a ring electrode assembly associated with the ICD of FIG. 3.

The third ring electrode assembly 130c can be coupled to the second multilumen member 162 such that the third electrode assembly 130c can also be disposed at the distal end 142 of the lead body 134, generally at a more distal point than the second electrode assembly 130b. The ring electrode assembly 130c can be generally cylindrical, and can include a ring electrode 132c, a third transmission member 136c, which comprises a third inner conductor 138c and a third insulative member 140c for the ring electrode 132c, a first sleeve 172 (FIG. 8A), and a second sleeve 174 (FIG. 8A). A tool 500 (FIG. 15) can be used to couple the ring electrode 132c to the first sleeve 172, as will be described herein. The first sleeve 172 can, in turn, couple the ring electrode 132c to the second multilumen member 162. Generally, the ring electrode 132c can be annular, and can be coupled to the lead assembly 116 so that the ring electrode 132c can be positioned adjacent to the heart 42 to receive electrical signals indicative of the electrical activity present in the particular portion of the heart 42. These electrical signals can then be transmitted to the ICD 110 via the inner conductor 138c of the transmission member 136c.

With reference to FIGS. 8-11, the first sleeve 172 can be formed of a suitable polymeric material, and can include a throughbore 176, a proximal end 178, a distal end 180, and a shoulder 182. The throughbore 176 of the first sleeve 172 can be sized to enable a portion of the fourth electrode assembly 130d to pass therethrough, such as the transmission member 136d, as will be described in greater detail herein. The proximal end 178 of the first sleeve 172 can couple the ring electrode 132c to the second multilumen member 162. Generally, the proximal end 178 can have a diameter that may be slightly smaller than the diameter of the second multilumen member 162, so that the proximal end 178 can be at least partially received within the second electrode assembly 130b. For example, the proximal end 178 can be received within the second defibrillator electrode 132b such that the proximal end 178 can be adjacent to and in contact with the second multilumen member 162 and the defibrillator electrode 132b can be adjacent to and in contact with the shoulder 182.

In one example, the proximal end 178 can include a stand-off 184, a first channel 186, and a second channel 188. The stand-off 184 can extend beyond the proximal end 178. The stand-off 184 can define a space between the proximal end 178 of the first sleeve 172 and an opposing end 190 of the second multilumen member 162 so that an adhesive X can be back-filled into the space to fixedly couple the first sleeve 172 to the second multilumen member 162. Alternatively, a separate tubing member could be inserted between the proximal end 178 and the second multilumen member 162 and adhesive can be back-filled into this separate tubing member to fixedly couple the first sleeve 172 to the second multilumen member 162.

The first channel 186 of the first sleeve 172 can be formed along a circumference of the proximal end 178, and can be spaced about twenty degrees to about thirty degrees from the stand-off 184. The first channel 186 can be shaped to accommodate a portion of the second defibrillator electrode 132b, and for example, the first channel 186 can receive at least a portion of the inner conductor 138b that can be coupled to the second defibrillator electrode 132b. The second channel 188 can be formed in the proximal end 178, and can be formed adjacent to the stand-off 184. In one example, the second channel 188 can extend from the proximal end 178 for a distance greater than the first channel 186, and typically, the second channel 188 can extend through and slightly beyond the shoulder 182. The second channel 188 can be shaped to accommodate a portion of the ring electrode 132c, such as the transmission member 136c of the ring electrode 132c.

The distal end 180 can support the ring electrode 132c, and can generally have a length that can be slightly longer than a length of the proximal end 178. The distal end 180 can include at least one annular rib 192, and as shown, preferably includes multiple ribs 192 separated by a plurality of channels 194, which can be defined between adjacent ones of the ribs 192. Each of the annular ribs 192 can extend a distance outwardly and above a surface 193 of the distal end 180, and each of the annular ribs 192 can generally circumscribe a circumference of the distal end 180. The annular ribs 192 can be spaced about equally apart from a distalmost end 195 of the first sleeve 172, and generally can be spaced so that adhesive can be applied in the respective channels 194 defined therebetween. Each of the ribs 192 can be spaced apart by about 0.015 inches to about 0.025 inches, however, any spacing could be employed depending upon the amount of adhesive desired to be applied between the ribs 192.

Figure 13:
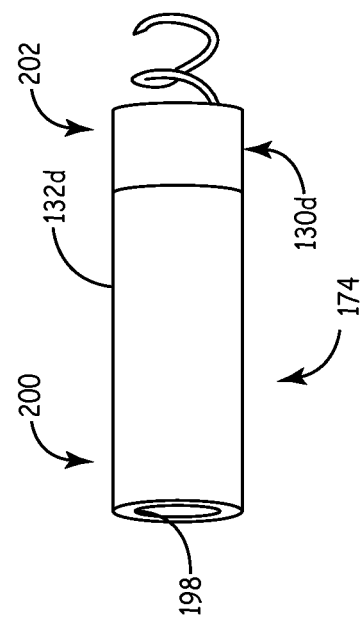
FIG. 13 is a perspective view of a second sleeve of the ring electrode assembly of FIG. 8A.

With reference to FIG. 13, generally, the ribs 192 can define three channels 194 (e.g., first channel 194a, second channel 194b, and third channel 194c). At least one of the three channels 194a, 194b, 194c can receive a liquid adhesive LA, which can couple the first sleeve 172 to the second sleeve 174, as will be discussed further herein. In one example, the first and second channels 194a, 194b can receive the liquid adhesive LA, while the third channel 194c can act as a well to receive any excess adhesive. In this way, excess adhesive will not be able to pool past the distalmost end 195 of the first sleeve 172 and contaminate the electrode. In addition, as the channels 194 are defined about the circumference of the first sleeve 172, the channels 194 can enable the formation of at least one 360 degree adhesive bond. Further, the ribs 192 can act as a guide for assisting an operator with applying a uniform amount of adhesive LA at the distal end 180 of the first sleeve 172. It should also be understood, that any combination of channels 194 can receive adhesive LA, so long as the second sleeve 174 is bonded to the first sleeve 172.

With reference again to FIGS. 8-11, the shoulder 182 can be formed between the proximal end 178 and the distal end 180, and can serve as a stop for the ring electrode 132c. In this regard, as will be discussed, the ring electrode 132c can be assembled onto the first sleeve 172 by sliding the ring electrode 132c from the distalmost end 195 over the ribs 192 so that the ring electrode 132c can be positioned adjacent to and about in contact with the shoulder 182. Generally, the shoulder 182 can have a diameter that may be about equal to the diameter of the ring electrode 132c so that the shoulder 182 and an outer surface 196 of the ring electrode 132c can form a substantially uniform surface. In addition, the shoulder 182 can direct a tensile load from the proximal end 144 of the lead assembly 116 to the tip electrode assembly 130d of the lead assembly 116. The ring electrode 132c can be coupled to the first sleeve 172, and can be received on the distal end 180 at a location adjacent to the shoulder 182. The third transmission member 136c can be disposed in the second channel 188 of the first sleeve 172, the third proximal conduit 154c of the first multilumen member 150, and the third distal conduit 170c of the second multilumen member 162, respectively.

With reference again to FIGS. 4-7, the tip electrode assembly 130d can be coupled to the second multilumen member 162 and can contact the anatomical structure at a distalmost part, such as the apex A of the heart 42. The tip electrode assembly 130d can include a tip electrode 132d, a fourth transmission member 136d, and the fixation member 166, if desired. A fourth inner conductor 138d can electrically couple the tip electrode 132d to the ICD 110 so that the tip electrode 132d can deliver a therapy, such as a pacing therapy, to the distalmost part of the anatomical structure.

The fixation member 166, if employed, can secure the lead assembly 116 to the anatomy, such as at the apex A of the heart 42. An exemplary fixation member 166 can be commercially available by Medtronic, Inc. of Minneapolis, Minn., and thus, the fixation member 166 will not be discussed in great detail herein. Briefly, however, as shown in FIG. 4, the fixation member 166 can comprise a helical screw 175 and a torque coil 177. As may be generally known, the helical screw 175 can be coupled to the torque coil 177, such that as a torque is applied to the torque coil 177, the helical screw 175 can be rotated to engage the anatomy. It should be noted that although an active fixation member 166 can be described and illustrated herein, a passive fixation member could be employed, if desired.

With continuing reference to FIGS. 4-7, the overlay 164 can extend between the first defibrillator electrode 132a and the second defibrillator electrode 132b. The overlay 164 can comprise a biocompatible polymer, such as a polyurethane silicon copolymer, but any suitable biocompatible polymer could be employed. The overlay 164 can generally have a thin wall thickness to compensate for the thickness of the first defibrillator electrode 132a to the second defibrillator electrode 132b. Thus, the overlay 164 can ensure that the lead assembly 116 can maintain the substantially uniform diameter D (FIG. 3) or can be an isodiametric lead assembly 116 between the first defibrillator electrode 132a and the second defibrillator electrode 132b. While the overlay 164 can ensure that the lead assembly 116 maintains the substantially uniform diameter D, it is also understood that the lead assembly 116 can be nonuniform.

Figure 21:
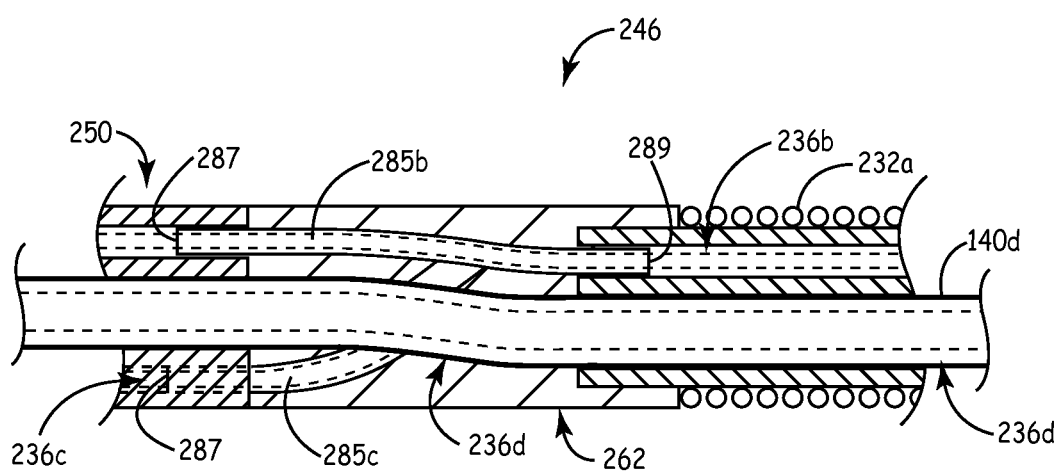
FIG. 21 is a cross-sectional view of an exemplary transition portion associated with the lead assembly of FIG. 19.

With reference now to FIG. 21 and in this example, the transition zone 146 can include at least one jumper member 185 for enabling the transmission members 136 to move relative to, and through, the multilumen members 150, 162. Generally, the transition zone 146 can include a jumper member 185 for each of the transmission members 136. Thus, in this example, the transition zone 146 can include a first jumper member 185a that may be sized to fit over the first transmission member 136a, a second jumper member 185b that may be sized to fit over the second transmission member 136b, and a third jumper member 185c that may be sized to fit over the third transmission member 136c. The jumper members 185 can be generally tubular in shape, and can be composed of a suitable polymeric material, such as a fluoropolymeric material.

Generally, the jumper members 185 can be configured to slidably receive each of the transmission members 136 and the conductor coil 136d, but the jumper members 185 can also be fixed to the first multilumen member 150 and the second multilumen member 162. Thus, the jumper members 185 can enable the transmission members 136 to move relative to, and through, the first multilumen member 150 and the second multilumen member 162. This can enable the lead assembly 116 to flex without damaging the electrode assemblies 130. In addition, the ability of the transmission members 136 to slide relative to the first multilumen member 150 and the second multilumen member 162 can enable the torque coil 177, if employed, to be rotated relative to the first multilumen member 150 and the second multilumen member 162 when securing the helical screw 175 to the anatomy. The jumper members 185 can generally be secured to the first and second multilumen members 150, 162 via a suitable adhesive.

For example, a first end 187 of each of the jumper members 185 can be inserted into the respective proximal conduit 154 of the first multilumen member 150, and then a second end 189 of each of the jumper members 185 can be received within the respective distal conduits 170 of the second multilumen member 162. Then, a suitable medical adhesive can be applied to an area that extends between the first multilumen member 150 and the second multilumen member 162 to secure the jumper members 185 to the first multilumen member 150 and the second multilumen member 162. Generally, the area can range from about 0.001 inches to about 0.150 inches, however, the area can vary depending upon the particular lead assembly 116. As previously described, the adhesive may be applied through any suitable process, such as back-filling. The suitable adhesive may also only be applied between the first and second multilumen members 150, 162.

Figure 8B:
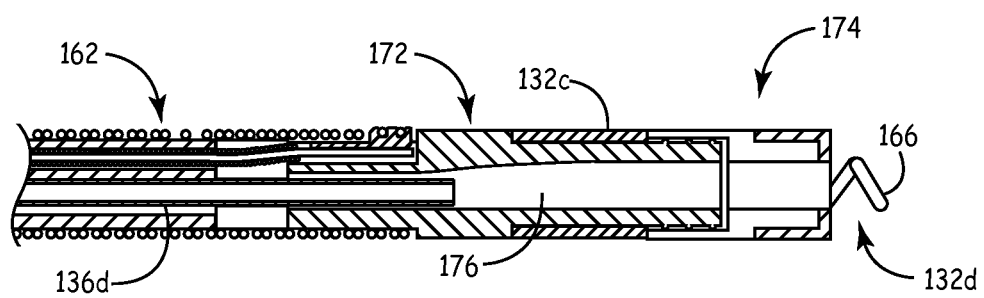
FIG. 8B is a cross-sectional view of the ring electrode assembly taken through line 8B-8B of FIG. 8A.

With reference to FIGS. 4, 8, and 13, the second sleeve 174 can be coupled to the first sleeve 172, adjacent the ring electrode 132c. The second sleeve 174 can be coupled to the first sleeve 172 via the adhesive LA applied to the channels 194. In this regard, the second sleeve 174 can include a throughbore 198, a proximal end 200, and a distal end 202. The throughbore 198 can be sized to have a diameter that can create an interference fit with the ribs 192 of the first sleeve 172 so that the second sleeve 174 can be press-fit and robustly bonded onto the distal end 180 of the first sleeve 172. Generally, the outer diameter of the throughbore 198 can be about equal to the diameter of the ring electrode 132c, so that the lead assembly 116 can be an isodiametric lead having the substantially uniform diameter D (FIG. 3).

The proximal end 200 can be configured to be coupled to the distal end 180 of the first sleeve 172. Generally, the proximal end 200 of the second sleeve 174 can be received onto the distal end 180 so that the proximal end 200 can be adjacent to the ring electrode 132c. The distal end 202 can be coupled to the tip electrode assembly 130d. As will be discussed, generally, at least a portion of the tip electrode assembly 130d can be received within the throughbore 198 at the distal end 202.

Figure 16:
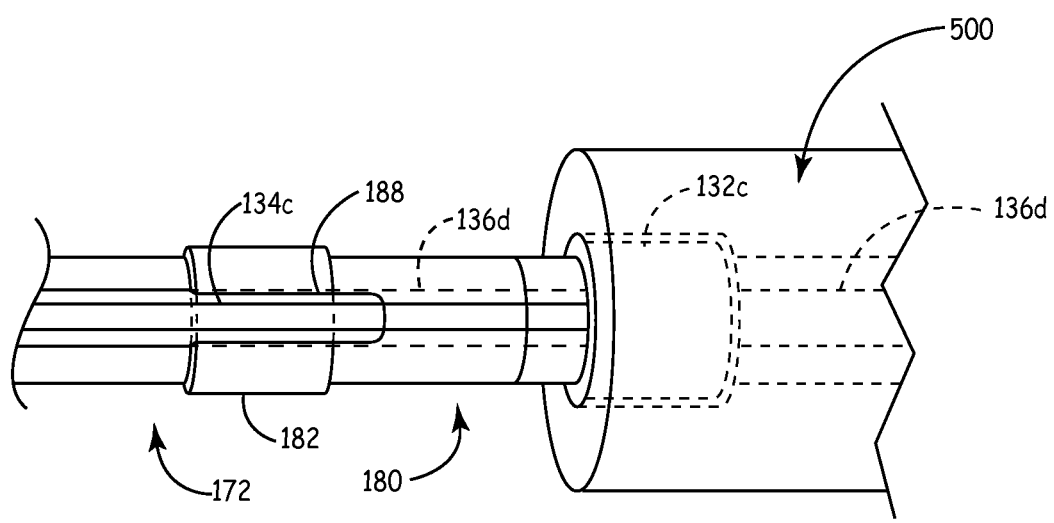
FIG. 16 is a schematic view of a tool for use in coupling the ring electrode to the first sleeve of FIG. 9.
Figure 17:
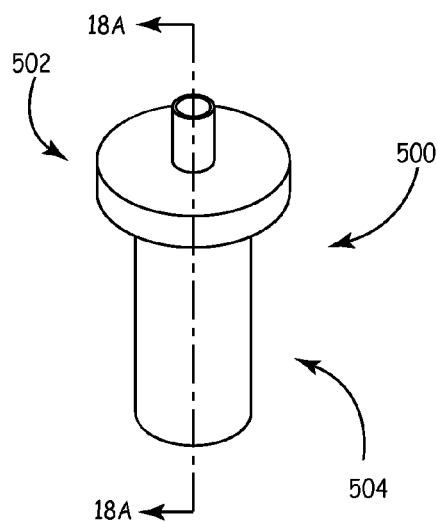
FIG. 17 is a perspective view of the tool of FIG. 16.

With reference to FIGS. 16-18, the tool 500 can be employed to secure the ring electrode 132c to the distal end 180 of the first sleeve 172. The tool 500 can include a first end 502 and a second end 504. While the tool 500 can generally be integrally formed, the tool 500 can also be formed through multiple post-processing or assembly steps. Generally, the tool 500 can be composed of a metal, metal alloy or polymeric material, such as an aluminum alloy or a polyetheretherketone material, but any suitable material or combination of materials could be employed. In addition, the tool 500 illustrated herein may be generally symmetric with respect to a central axis C, however, the tool 500 can have any desired shape so long as the tool 500 can properly seat the ring electrode 132c on the first sleeve 172.

With reference to FIGS. 16-18, the first end 502 can include a flange 506 and a projection 508. The flange 506 can be annular and can define a throughbore 510, which can extend through a first side 512 to an underside 514 of the flange 506. The throughbore 510 can be sized to receive a tooling rod therethrough. The receipt of the tooling rod through the throughbore 510 can enable the tool 500 to be positioned about the distal end 180 of the first sleeve 172. The projection 508 can also be annular and can have an outer diameter D1 that may be about 4 to 6 times smaller than an outer diameter D2 of the flange 506. Generally, the projection 508 can have a length L1 that may be about 1.5 to 2 times longer than a length L2 of the flange 506. The projection 508 can include a bore 516, which can extend over the length L1 of the projection 508 from a first end 518 of the projection 508 to a second end 520 of the projection 508. In one example, the bore 516 can comprise a counterbore 521, which can define a first interior surface 522. The remainder of the bore 516 at the second end 520 of the projection 508 can define a second interior surface 524.

The first interior surface 522 of the projection 508 can be formed adjacent to the first end 518 of the projection 508 and can have a diameter D3 that can generally be sized to receive the ring electrode 132c. The second interior surface 524 can be formed adjacent to the second end 520 of the projection 508 and can have a diameter D4 that can generally be sized to enable the tool 500 to slidably receive the distal end 180 of the first sleeve 172. Generally, the second interior surface 524 can extend for a length L4, which can be substantially longer than a length L3 of the first interior surface 522. The length L3 of the first interior surface 522 can be sized to correspond to a length L of the ring electrode 132c (FIG. 8A), while the length L4 of the second interior surface 524 can be sized to enable the tool 500 to receive a desired length of the distal end 180 within the second interior surface 524.

In this regard, with reference to FIGS. 16-18, the length L4 of the second interior surface 524 can be sized so that the tool 500 can only receive a selected length of the distal end 180, which can ensure that the ring electrode 132c may be substantially positioned in the same location on the first sleeve 172 during manufacturing of the lead assembly 116. In addition, as the throughbore 510 can have a diameter that may be smaller than the diameter of the distal end 180 of the first sleeve 172, the distalmost end 195 of the first sleeve 172 can contact the flange 506 at the second end 520 of the projection 508 when the ring electrode 132c is properly seated adjacent to the shoulder 182. The contact between the distalmost end 195 of the first sleeve 172 and the flange 506 or the ring electrode 132c contacting the shoulder 182 can provide tactile feedback to the operator, via a positive stop, that the ring electrode 132c is properly positioned.

Figure 18C:
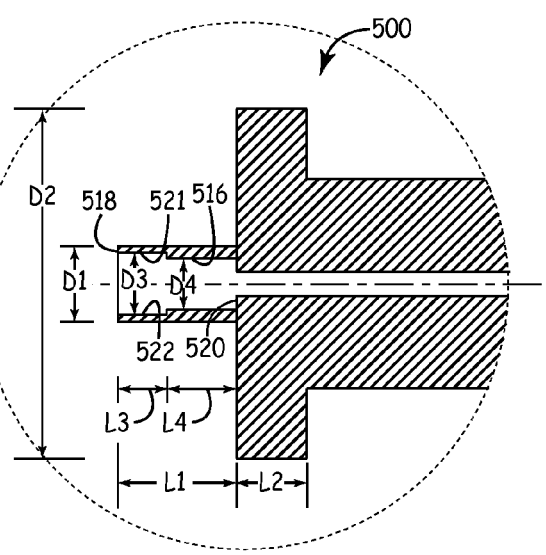
FIG. 18C is a detail view of a flange portion of the tool of FIG. 17.
Figure 18A:
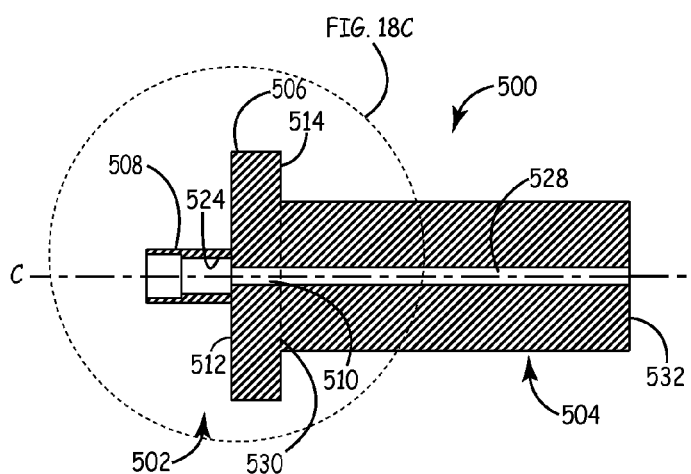
FIG. 18A is a cross-sectional view of the tool of FIG. 17, taken along line 18A-18A of FIG. 17.
Figure 18B:
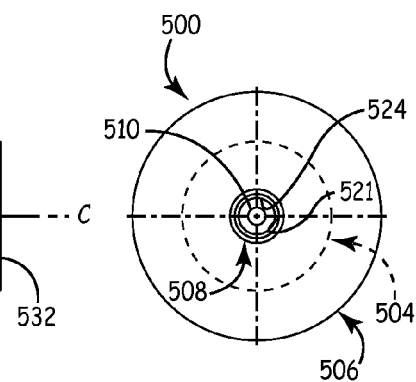
FIG. 18B is an end view of FIG. 18A.

With reference to FIGS. 18A and 18B, the second end 504 of the tool 500 can be cylindrical and can provide the operator with a graspable portion or handle for using the tool 500. Although not illustrated herein, the second end 504 can also include a knurled or roughened surface to enable the operator to easily grasp the tool 500. The second end 504 can include a throughbore 528, which can extend from a first side 530 to a second side 532 of the second end 504. The throughbore 528 can have a diameter that may be about equal to the diameter of the throughbore 510 of the flange 506. The first side 530 of the second end 504 can be adjacent to the underside 514 of the flange 506. As will be discussed further herein, the tool 500 can enable the ring electrode 132c to be coupled to the first sleeve 172.

An exemplary assembly process for the lead assembly 116 will now be described with reference to FIGS. 4-18. It should be understood, however, that the order of the operations may be altered to arrive at a similar final product.

Figure 12:
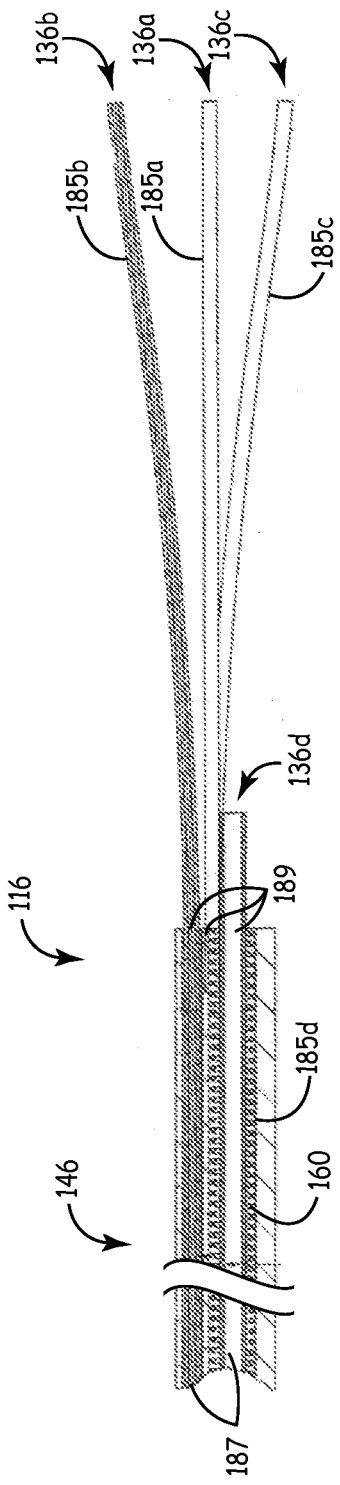
FIG. 12 is a cross-sectional view of an exemplary transition portion associated with the lead assembly of FIG. 4.
Figure 15:
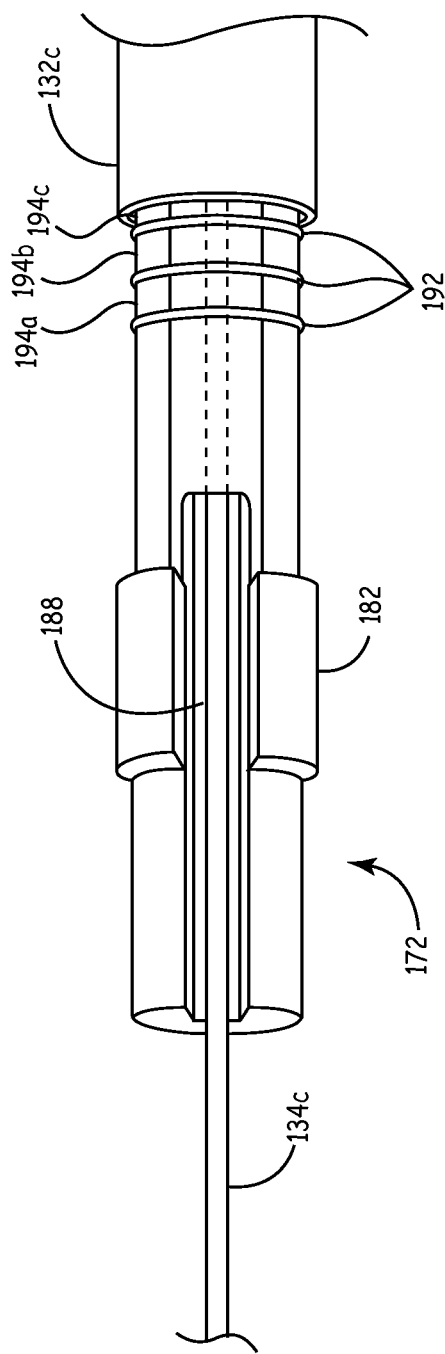
FIG. 15 is a schematic view of the first sleeve of FIG. 9 with a ring electrode partially coupled to the first sleeve according to various examples.

The support coil 160 can be coupled to the fourth conduit 154d of the first multilumen member 150 (FIG. 5). The jumper members 185 can be inserted into the first multilumen member 150 (FIG. 12). The second multilumen member 162 can then be positioned such that the second end 189 of the jumper members 185 can be received into the second multilumen member 162 (FIG. 12). A suitable medical adhesive can then be applied, through any suitable process, such as back-filling, to secure the jumper members 185 to the first multilumen member 150 and the second multilumen member 162. With the first multilumen member 150 secured to the second multilumen member 162, the defibrillator electrodes 132a, 132b can be positioned on the second multilumen member 162 and the transmission members 136 can then be inserted through the lead assembly 116 (FIG. 4). Next, the overlay 164 can be formed on, applied to, or extruded onto the second multilumen member 162. Next, the ring electrode 132c can be coupled to the first sleeve 172 (FIG. 15).

In this regard, the proximal end 178 of the first sleeve 172 can be coupled to the opposing end 190 of the second multilumen member 162, via an adhesive, for example (FIG. 8A). Then, the ring electrode 132c can be positioned on the distalmost end 195 of the first sleeve 172 (FIG. 15). Next, the tool 500 can be slid over the transmission member 136d and positioned over the ring electrode 132c (FIG. 16). Generally, the tool 500 can be positioned such that the ring electrode 132c can be received within the first interior surface 522. Then, the operator can apply a force to the tool 500 to push the ring electrode 132c from the distalmost end 195 towards the shoulder 182.

As the tool 500 advances forward, the ring electrode 132c can contact the first interior surface 522 of the projection 508 (FIG. 18C). Further advancement of the tool 500 relative to the first sleeve 172 can cause the ring electrode 132c to be advanced toward the shoulder 182, with the distal end 180 of the first sleeve 172 being received within the second interior surface 524. The operator can advance the tool 500 from the distalmost end 195 towards the shoulder 182 until the distalmost end 195 contacts the second end 520 of the projection 508 (FIG. 18C). Once the distalmost end 195 contacts the second end 520 of the projection 508, the ring electrode 132c cannot be further advanced relative to the first sleeve 172, which thereby results in a repeatable placement of the ring electrode 132c on the first sleeve 172 (FIG. 8A).

Figure 14:
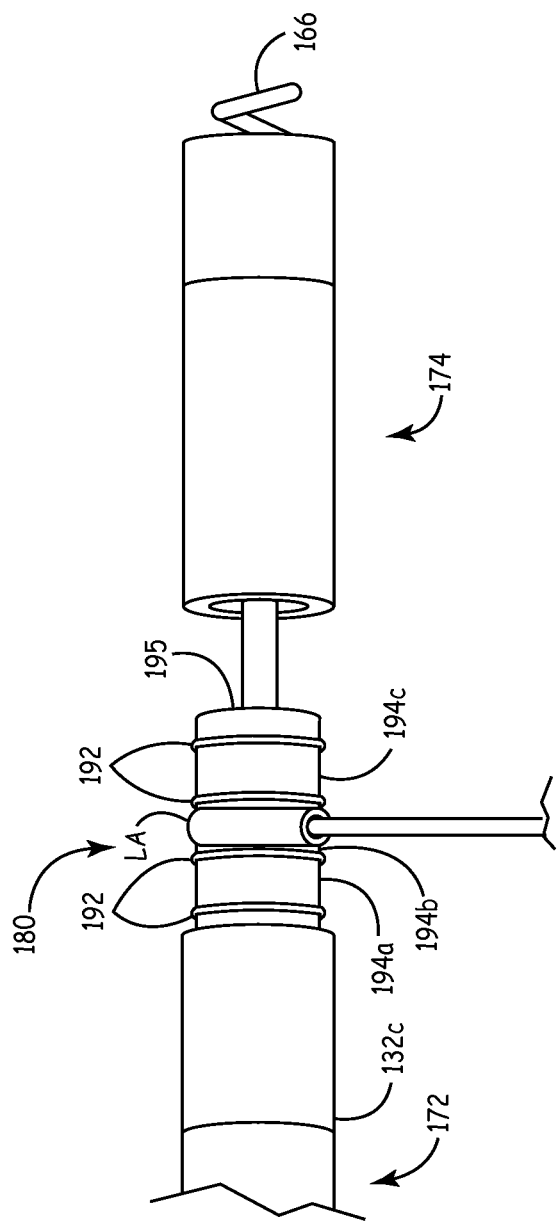
FIG. 14 is a schematic view of a technique used to couple the second sleeve to the first sleeve of the ring electrode assembly of FIG. 8A.

With the ring electrode 132c positioned on the first sleeve 172, generally at least the first two channels 194a, 194b can be exposed (FIG. 14). Then, the liquid adhesive LA can be applied about the circumference of the first sleeve 172 in the first channel 194a and the second channel 194b. The operator can then push the proximal end 200 of the second sleeve 174 onto the distal end 180 of the first sleeve 172 (FIG. 8A). Generally, the operator can push the second sleeve 174 onto the first sleeve 172 until the second sleeve 174 is adjacent to the ring electrode 132c (FIG. 8A).

With the lead assembly 116 assembled, it can then be coupled to the ICD 110 and implanted into the anatomical structure (FIG. 3). Generally, the lead assembly 116 can be implanted such that the first defibrillator electrode 132a can be adjacent to the superior vena cava 44 or within the right atrium C, the second defibrillator electrode 132b can be within the right ventricle B, and the tip electrode 132d can be adjacent to the apex A of the heart 42 (FIG. 3).

Figure 19:
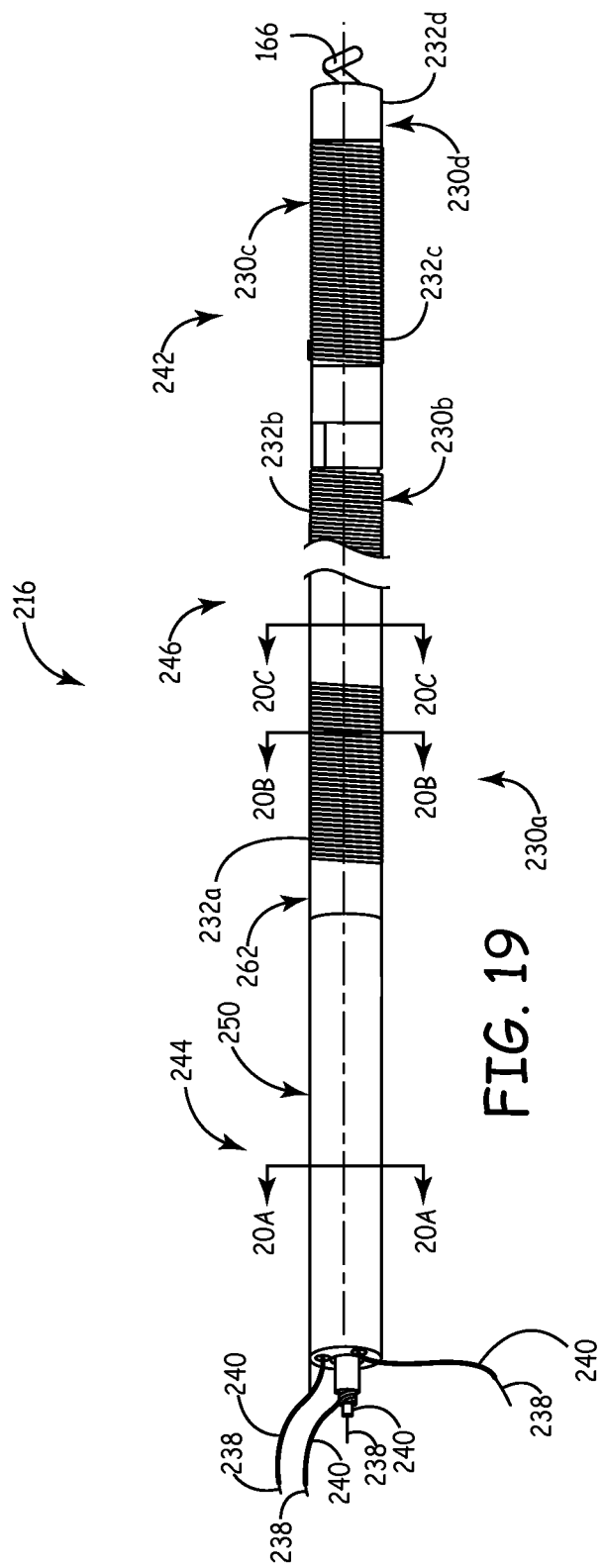
FIG. 19 is a perspective schematic view of one of various exemplary lead assemblies according to the present teachings.

In another example as shown in FIGS. 19-21, a lead assembly 216 can be employed with the ICD 110. As the lead assembly 216 can be similar to the lead assembly 116 described with reference to FIGS. 3-16, only the differences between the lead assembly 116 and the lead assembly 216 will be discussed in great detail herein, and similar reference numerals will be used to denote the same or similar components.

With reference to FIG. 19, the lead assembly 216 can include a distal end 242, a proximal end 244, a transition zone 246 for transitioning the lead assembly 216 between the distal end 242 and the proximal end 244, a first multilumen tubing member 250, and a second multilumen tubing member 262. Similarly to that already described, the distal end 242 can include electrode assemblies 230 having associated electrodes 232 and transmission members 236, comprising inner conductors 238 and insulative members 240.

The proximal end 244 of the lead assembly 216 can be stiffer than the distal end 242 of the lead assembly 216 to enable the lead assembly 216 to be positioned within the anatomical structure, while providing strain relief. In addition, the proximal end 244 of the lead assembly 216 can have a different conduit layout than the distal end 242 to protect against bending and flexing. The proximal end 244 of the lead assembly 216 can also interact with the connector assembly 114 as previously described.

Generally, the first multilumen member 250 can be composed of a biocompatible material, such as a biocompatible polymer, for example, a silicone rubber. In one example, the first multilumen member 250 can comprise a biocompatible polymer with additional structural support or stiffness, such as a high molecular weight polyurethane based polymer or high molecular weight silicone. The additional structural support in the composition of the first multilumen member 250 can further stiffen the proximal end 244 of the lead assembly 216. Further, when the transmission members 236 are generally placed down the center of the lead assembly 216, the transmission members 236 can experience less strain.

Figure 20A:
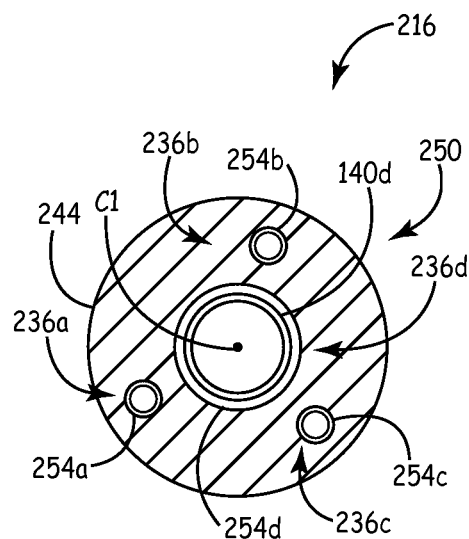
FIG. 20A is a cross-sectional view of the lead assembly of FIG. 19, taken along line 20A-20A of FIG. 19.
Figure 20B:
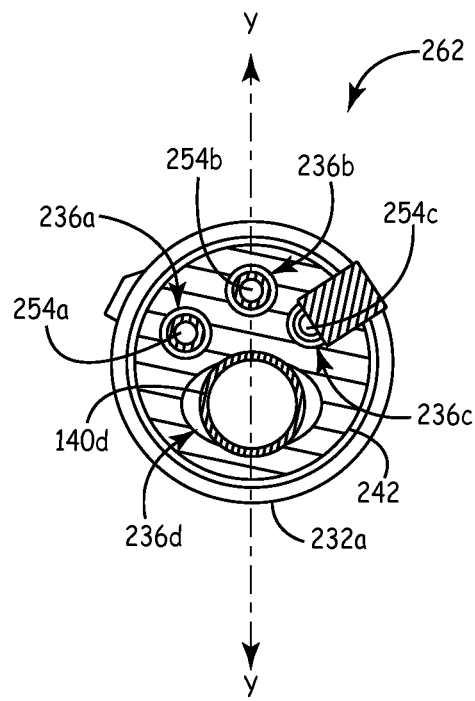
FIG. 20B is a cross-sectional view of the lead assembly of FIG. 19, taken along line 20B-20B of FIG. 19.
Figure 20C:
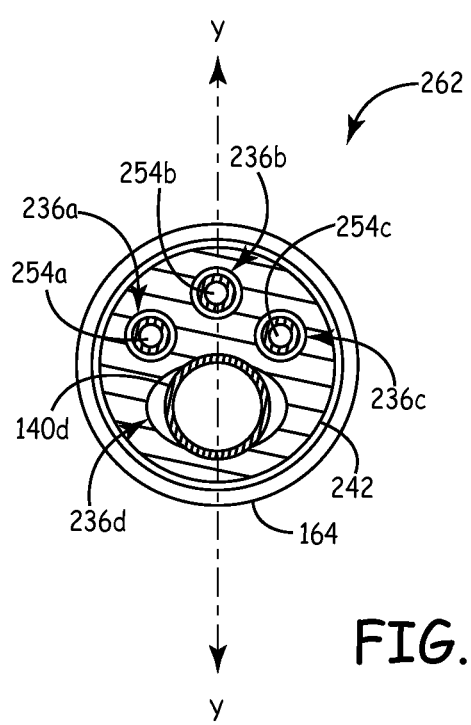
FIG. 20C is a cross-sectional view of the lead assembly of FIG. 19, taken along line 20C-20C of FIG. 19.

With reference to FIGS. 20A-20C, the first multilumen member 250 can comprise at least one separate proximal conduit 254 for each inner conductor 238, and for example, the first multilumen member 250 can comprise a first proximal conduit 254a, a second proximal conduit 254b, a third proximal conduit 254c, and a fourth proximal conduit 254d. In this example, the first proximal conduit 254a, second proximal conduit 254b, and third proximal conduit 254c can have a diameter that can be smaller than a diameter of the fourth proximal conduit 254d.

Typically, the proximal conduits 254 can be positioned within the first multilumen member 250 such that the first multilumen member 250 can be symmetric with respect to a central axis or centerline C1 of the lead assembly 216. In this regard, the fourth proximal conduit 254d can be positioned about the centerline C1 of the lead assembly 216. The centerline C1 can also comprise a neutral axis for the lead assembly 216, so that all forces applied through the fourth proximal conduit 254d to position the lead assembly 216 can be equally distributed about the lead assembly 216. The equal distribution of forces can provide the lead assembly 216 with strain relief if the lead assembly 216 is bent. Further, by positioning the fourth proximal conduit 254d about the centerline C1, the stiffness of the proximal end 244 can be increased without the use of additional components.

With the fourth proximal conduit 254d positioned about the centerline C1 of the lead assembly 216, the first, second, and third proximal conduits 254a, 254b, 254c can be spaced equally about and apart from a circumference of the fourth proximal conduit 254d. The placement of the proximal conduits 254 can enable the proximal end 244 of the lead assembly 216 to be balanced, in contrast to the distal end 242 of the lead assembly 216, which can facilitate the insertion of the lead assembly 216 into the anatomy. The proximal conduits 254 can receive each of the transmission members 236 of the electrode assemblies 230 to guide each of the transmission members 236 from the ICD 110 to the associated electrodes 232 of the respective electrode assembly 230.

With reference to FIG. 21, the transition zone 246 can include at least one jumper member 285 for enabling the transmission members 236 to move relative to and through, the multilumen members 250, 262. The jumper members 285 can be generally tubular in shape, and can be composed of a suitable polymeric material, such as a fluoropolymeric material. Generally, the number of jumper members 285 corresponds to the number of transmission members 236. Thus, in this example, the transition zone 246 can include a first jumper member 285a that may be sized to fit over a first transmission member 236a, a second jumper member 285b that may be sized to fit over a second transmission member 236b, a third jumper member 285c that may be sized to fit over a third transmission member 236c, and a fourth jumper member 285d that may be sized to fit over a fourth transmission member 236d.

With reference to FIGS. 19-21A, the jumper members 285 can be configured to slidably receive each of the transmission members 236. Typically, the jumper members 285 can be flexible to enable the transmission members 236 to be routed into appropriate distal conduits 270 associated with the distal end 242 of the lead assembly 216. Thus, the jumper members 285 can enable the transmission members 236 to move relative to, and through, the first multilumen member 250 and the second multilumen member 262. This can enable the lead assembly 216 to flex without damaging the electrode assemblies 230. Accordingly, the lead assembly 216 can provide improved stiffness with strain relief to facilitate the insertion and implantation of the lead assembly 216 within the anatomical structure.

In this regard, the proximal conduits 254 are symmetric with respect to the centerline C1 in the proximal end 244, but can be symmetric with respect to the axis Y at the distal end 242, which is substantially perpendicular to the centerline C1 (as shown in FIG. 20B). Thus, the jumper members 285 can allow the transmission members 236 to transition into conduits 270 that are located in different positions than the conduits 254 of the proximal end 244.

An exemplary assembly process for the lead assembly 216 will now be described with reference to FIGS. 19-21A. It should be understood, however, that the order of the operations may be altered to arrive at a similar final product.

Initially, the jumper members 285 can be fixed relative to the first and second multilumen members 250, 262. As such, a first end 287 of each of the jumper members 285 can be inserted into the respective proximal conduit 254 of the first multilumen member 250, and then a second end 289 of each of the jumper members 285 can be received within the respective distal conduit 270 of the second multilumen member 262.

Figure 21A:
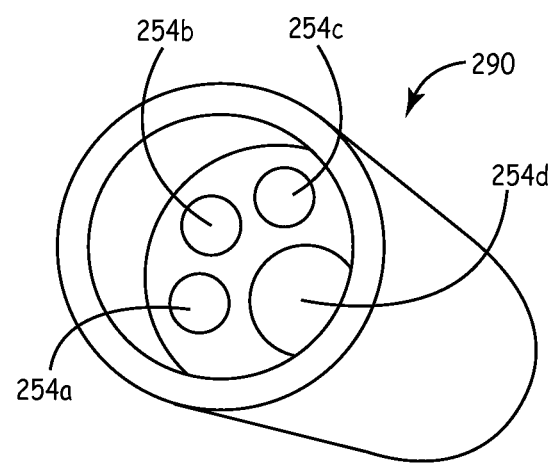
FIG. 21A is a simplified perspective view of the transition portion of FIG. 21.

Then, an adhesive can be applied to an area that extends between the first multilumen member 250 and the second multilumen member 262 to secure the jumper members 285 to the first multilumen member 250 and the second multilumen member 262, as previously described. In one example, however, as best shown in FIG. 21A, a molded component 290 could be positioned between the first multilumen member 250 and the second multilumen member 262. The molded component 290 could guide and support the jumper members 285, and could be coupled to the first multilumen member 250 and the second multilumen member 262 via a suitable fastening technique, such as adhesive bonding, press-fitting, etc.

After the first multilumen member 250 is secured to the second multilumen member 262, the electrode assemblies 230 can be assembled as previously described. With the lead assembly 216 assembled, it can then be coupled to the ICD 110 and implanted into the anatomical structure as shown in FIG. 3. For example, the lead assembly 216 can be implanted such that the electrodes 232 can be adjacent to the superior vena cava 44, within the right atrium C, within the right ventricle B, and/or adjacent to the apex A of the heart 42.

Figure 22:
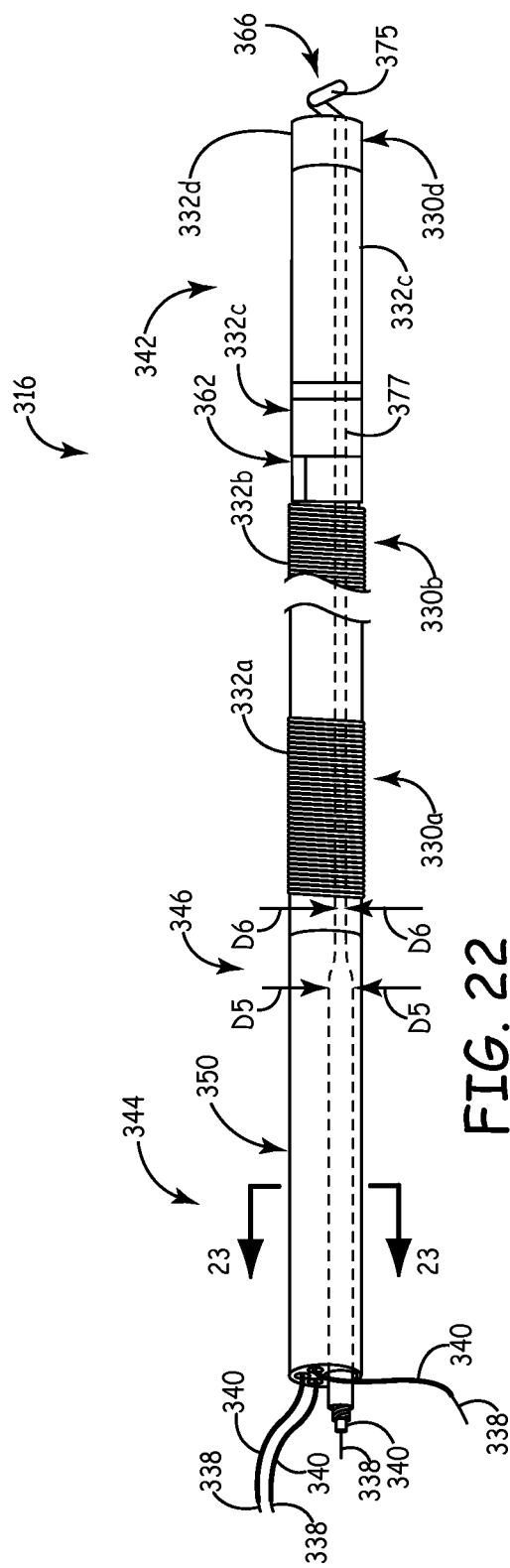
FIG. 22 is a perspective schematic view of one of various exemplary lead assemblies according to the present teachings.
Figure 23:
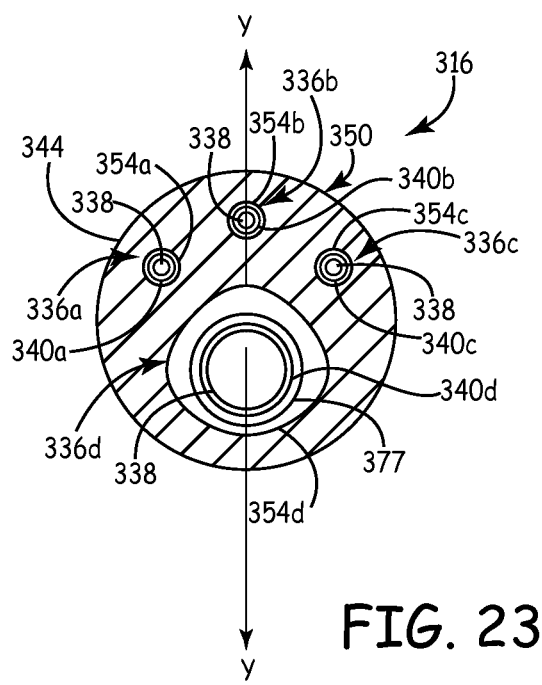
FIG. 23 is a cross-sectional view of the lead assembly of FIG. 22, taken along line 23-23 of FIG. 22.
Figure 24:
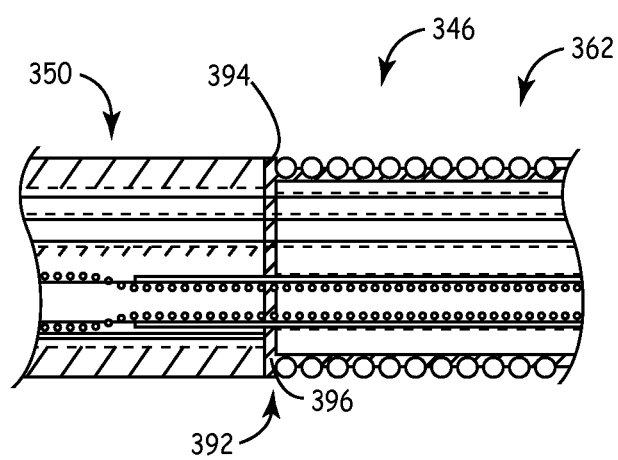
FIG. 24 is a cross-sectional view of an exemplary transition portion associated with the lead assembly of FIG. 22.
Figure 25:
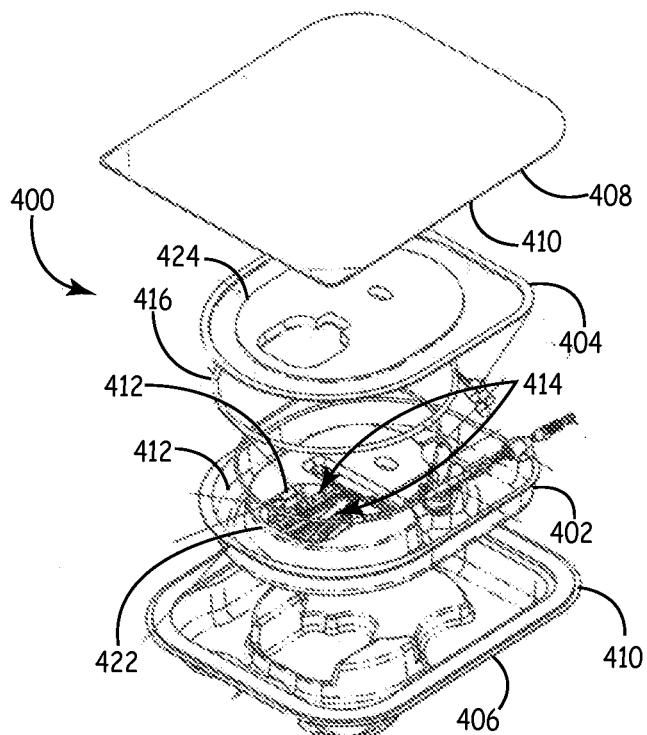
FIG. 25 is an exploded view of one of an exemplary packaging system for use with the cardiac lead assembly of FIGS. 4, 19, and 22.
Figure 26:
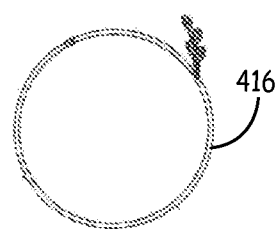
FIG. 26 is a perspective view of a plurality of exemplary stylets that can be packaged with the cardiac lead assembly of FIGS. 4, 19, and 22.
Figure 27:
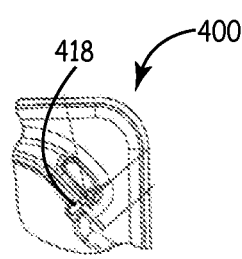
FIG. 27 is a bottom view of an inner tray of the packaging system of FIG. 25.
Figure 28:
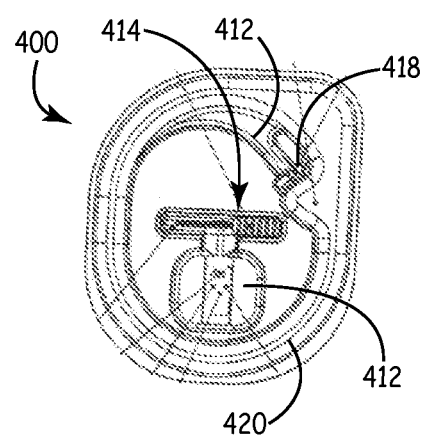
FIG. 28 is a detail view of a tip protector of the inner tray of FIG. 25 coupled to a portion of the cardiac lead system of FIGS. 4, 19, and 22.

In another example as shown in FIGS. 22-24, a lead assembly 316 can be employed with the ICD 110. As the lead assembly 316 can be similar to the lead assembly 116 described with reference to FIGS. 3-16, only the differences between the lead assembly 116 and the lead assembly 316 will be discussed in great detail herein, and similar reference numerals will be used to denote the same or similar components.

With reference to FIG. 22, the lead assembly 316 can include a distal end 342, a proximal end 344, a transition zone 346 for transitioning the lead assembly 316 between the distal end 342 and the proximal end 344, a first multilumen tubing member 350, and a second multilumen tubing member 362. Similarly to that already described, the distal end 342 can include electrode assemblies 330 having associated electrodes 332 and transmission members 336, comprising inner conductors 338 and insulative members 340. In this example, the insulative members 340 can comprise two insulative tubes, each having different inside diameters such that insulative members 340 can overlap each other to form a stepped insulation that substantially matches the stepped shape of the transition zone 346.

The distal end 342 of the lead assembly 316 can include the second multilumen member 362, the electrode assemblies 330, and a fixation member 366. The fixation member 366 can secure the lead assembly 316 to the anatomical structure, such as the apex A of the heart 42 (FIG. 3). The fixation member 366 can be similar to the fixation member 166 and, therefore, will not be discussed in detail herein. Briefly, however, the fixation member 366 can include a helical screw 375 and a torque coil 377. As may be generally known, the helical screw 375 can be coupled to the torque coil 377, such that as a torque is applied to the torque coil 377, the helical screw 375 can be rotated to engage the anatomical structure. It should be noted that although the fixation member 366 as described and illustrated herein employs active fixation, passive fixation could also be employed.

The proximal end 344 of the lead assembly 316 can be stiffer than the distal end 342 of the lead assembly 316 to enable the lead assembly 316 to be positioned within the anatomical structure, while providing strain relief. The proximal end 344 of the lead assembly 316 can also interact with the connector assembly 114 as previously described.

Generally, the first multilumen member 350 can be composed of a biocompatible material, such as a biocompatible polymer (e.g., a silicone rubber). In one example, the first multilumen member 350 can comprise a biocompatible polymer with additional structural support or stiffness, such as a high molecular weight polyurethane based polymer, high molecular weight silicone, etc. The additional structural support in the composition of the first multilumen member 350 can further stiffen the proximal end 344 of the lead assembly 316.

With reference to FIGS. 22 and 23, the first multilumen member 350 can include at least one separate proximal conduit 354 for each inner conductor 338, and for example, the first multilumen member 350 can comprise a first proximal conduit 354a, a second proximal conduit 354b, a third proximal conduit 354c, and a fourth proximal conduit 354d. In this example, the first proximal conduit 354a, second proximal conduit 354b, and third proximal conduit 354c can have a diameter that can be smaller than a diameter of the fourth proximal conduit 354d. Further, the first proximal conduit 354a, second proximal conduit 354b and third proximal conduit 354c can be positioned in the substantially same position as the first proximal conduit 154a, second proximal conduit 154b and third proximal conduit 154c of the lead assembly 116, and thus, the proximal end 344 of the lead assembly 316 can also be symmetrical with respect to the axis Y. The fourth proximal conduit 354d, however, can have a diameter that can be slightly larger than the diameter of the fourth proximal conduit 154d of the lead assembly 116 and/or the fourth proximal conduit 354d may have an irregular shape, as illustrated.

The larger diameter of the fourth proximal conduit 354d can allow for receipt of a correspondingly large diameter torque coil 377. The torque coil 377 can comprise a suitable biocompatible coil, which can extend from the proximal end 344 of the lead assembly 316 to the distal end 342 of the lead assembly 316 through the respective fourth conduits 354d, 370d. The torque coil 377 can have a first diameter D5 throughout the fourth proximal conduit 354d at the proximal end 344 and can transition at the transition zone 346 to a second diameter D6, which is maintained throughout the fourth distal conduit 170d of the distal end 342. Generally, the torque coil 377 can transition between the first diameter D5 and the second diameter D6 adjacent to a distalmost portion of the proximal end 344. In one example, the torque coil 377 can be stepped gradually from the first diameter D5 to the second diameter D6 such that the torque coil 377 exits the proximal end 344 at the diameter D6. In this regard, the torque coil 377 will pass through the transition zone 346 with a constant diameter (e.g., second diameter D6).

It should be understood, however, that alternate embodiments can be used to obtain the same result. For example, instead of the single torque coil 377, two coils of differing diameters could be coupled together via a suitable mechanism, such as a sleeve, welding, etc., to reduce stress on the proximal end 344 of the lead assembly 316.

In general, however, the first diameter D5 is greater than the second diameter D6 to reduce the stress acting on the proximal end 344 of the lead assembly 316. The larger diameter D5 of the torque coil 377 in the proximal end 344 can inherently be at a lower stress state, thereby reducing the stress on the proximal end 344 of the lead assembly 316. The larger diameter D5 of the torque coil 377 in the proximal end 344 can provide strain relief for the torque coil 377, itself. In effect, the larger diameter D5 of the torque coil 377 in the proximal end 344 provides appropriate flex characteristics for exo-cardiac movement, while the reduced diameter D6 of the torque coil 377 in the distal end 342 provides appropriate flex characteristics for inter-cardiac movement. Both flex characteristics can be achieved while still transferring torque to concurrently allow for extension and retraction of the helical screw 375. Typically, the first diameter D5 can be from about 0.001 inches to about 0.010 inches greater than the second diameter D6.

Referring now to FIG. 24, the transition zone 346 can comprise a joint 392. The joint 392 may be illustrated herein as a butt joint, however, any joint could be employed to couple the first multilumen member 350 to the second multilumen member 362. As illustrated, a proximal end face 394 of the first multilumen member 350 can be positioned directly adjacent to a distal end face 396 of the second multilumen member 362 and a suitable adhesive, such as a medical grade liquid adhesive, can be back-filled into the joint 392 to bond the first multilumen member 350 to the second multilumen member 362, and in turn, the proximal end 344 to the distal end 342.

As the proximal end 344 of the lead assembly 316 can be stiffer than the distal end 342 of the lead assembly 316, the lead assembly 316 can be easily passed through the anatomical structure and implanted in the desired location in the anatomical structure, such as in the heart 42 (FIG. 3). In addition, the increased flexibility of the distal end 342 allows the distal end 342 to bend and flex for absorbing any strain placed on the lead assembly 316 while the lead assembly 316 remains within the anatomical structure. Further, the transition zone 346 can enable the transmission members 336 to move relative to the lead assembly 316 as the lead assembly 316 flexes or bends, thereby reducing strain on the electrode assemblies 330.

With reference now to FIGS. 25-28, an exemplary packaging system 400 for use with the cardiac lead assembly 116, 216, 316 of the various figures is illustrated. The packaging system 400 can include an inner tray 402, an inner lid 404, an outer tray 406, and an outer lid 408. The outer tray 406 and the outer lid 408 can be hermetically joined and sealed along corresponding outer peripheries 410 for air-tight containment of the cardiac lead assembly 116, 216, 316 of the IMD 10 after manufacture and during transportation to the operating room before implantation in the patient 40.

The inner tray 402 can include a plurality of voids 412 for receiving various components of the IMD 10. In particular, the plurality of voids 412 may be shaped to retain the lead assembly 116, 216, 316, various tools for implantation 414, a stylet 416, etc. The plurality of voids 412 may comprise a tip protector 418, a stylet void 420, and a lead assembly void 422. The tip electrodes 36a, 36b of the IMD 10 may be removably positioned within the tip protector 418. As such, the tip protector 418 can fixedly retain at least one of the electrode assemblies 130, 230, 330 and the fixation member 166, 366 as discussed above. Likewise, the stylet 416 may be removably positioned within the stylet void 420 and the lead assembly 116, 216, 316 may be removably positioned within the lead assembly void 422. Accordingly, the stylet 416 and lead assembly 116, 216, 316 may be retained through protrusions 424 in the inner lid 404.

While specific examples have been described in the specification and illustrated in the drawings, it will be understood by those of ordinary skill in the art that various changes may be made and equivalents may be substituted for elements thereof without departing from the scope of the present disclosure. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. An implantable medical device, comprising:
   a body assembly that provides at least one electrical signal corresponding to a therapy; and
   a cardiac lead assembly having a proximal portion, a transition zone and a distal portion, the proximal portion in communication with the body assembly to receive the therapy and the distal portion adapted to be coupled to an anatomical structure to transmit the at least one electrical signal to the anatomical structure, the proximal portion having a first stiffness and the distal portion having a second stiffness,
   wherein the first stiffness is greater than the second stiffness
   wherein said proximal portion comprises a first multilumen tubing member having a plurality of longitudinally extending lumens and which extends from the body assembly to the transition zone and the distal portion comprises a second multilumen tubing member having a like plurality of longitudinally extending lumens and which extends from the transition zone to a distal portion of the cardiac lead assembly; and
   wherein at least one of the lumens in the first tubing member is not axially aligned with any of the lumens of the second tubing member.

2. The implantable medical device of claim 1, wherein the transition zone is located between the proximal portion and the distal portion, and wherein the transition zone comprises a lumen connecting the at least one axially non-aligned lumen of the first tubing member to a lumen of the second tubing member.

3. The implantable medical device of claim 1, wherein the first multilumen member comprises a first biocompatible polymer and the second multilumen member comprises a second biocompatible polymer, and the second biocompatible polymer is different from the first biocompatible polymer.

4. The implantable medical device of claim 3, wherein the first biocompatible polymer is one of a high molecular weight polyurethane based polymer, a high molecular weight silicone, and combinations thereof, and the second biocompatible polymer is a different one of a high molecular weight polyurethane based polymer, a high molecular weight silicone, and combinations thereof.

5. The implantable medical device of claim 3, wherein the second biocompatible polymer comprises a silicon copolymer.

6. The implantable medical device of claim 1, wherein the cardiac lead assembly further comprises:
   at least one electrode assembly and a transmission member that extends from the body assembly to the at least one electrode assembly to conduct the at least one electrical signal from the body assembly to the at least one electrode.

7. The implantable medical device of claim 6, wherein the transmission member includes a support structure at the proximal portion that provides hoop strength to the proximal portion of the cardiac lead assembly.

8. The implantable medical device of claim 7, wherein the support structure is at least one of a support coil, a polymer tubing, and a braided sheath.

9. The implantable medical device of claim 7, wherein the support structure is conductive.

10. The implantable medical device of claim 1, wherein the body assembly comprises an implantable pulse generator, an implantable cardioverter-defibrillator, cardiac resynchronization therapy defibrillator or combinations thereof.

* * * * *